United States Patent
Smith, III et al.

(10) Patent No.: US 7,767,142 B1
(45) Date of Patent: Aug. 3, 2010

(54) MEDICAL WASTE PROCESSOR AND PROCESSING METHOD

(75) Inventors: Otley L. Smith, III, El Paso, TX (US); R. Mason Bryant, Loveland, CO (US)

(73) Assignee: Oncore Technology, LLC, Grand Prairie, TX (US)

( * ) Notice: Subject to any disclaimer, the term of this patent is extended or adjusted under 35 U.S.C. 154(b) by 634 days.

(21) Appl. No.: 11/639,084

(22) Filed: Dec. 14, 2006

Related U.S. Application Data

(60) Provisional application No. 60/750,170, filed on Dec. 14, 2005.

(51) Int. Cl.
- *A61L 2/18* (2006.01)
- *A61L 9/00* (2006.01)
- *B01J 8/08* (2006.01)
- *B02C 7/00* (2006.01)

(52) U.S. Cl. .............................. 422/37; 422/32; 422/29; 422/28; 422/209; 422/224; 422/239; 422/292; 422/300; 241/299; 241/606

(58) Field of Classification Search .................... 422/28, 422/29, 32, 37, 209, 224, 239, 292, 300; 241/299, 606
See application file for complete search history.

(56) References Cited

U.S. PATENT DOCUMENTS

| 5,119,994 | A | * | 6/1992 | Placzek | 241/17 |
| 6,042,802 | A | * | 3/2000 | Drake | 423/477 |
| 6,171,558 | B1 | | 1/2001 | Simpson | |
| 7,032,322 | B1 | | 4/2006 | Smith | |
| 2006/0278741 | A1 | * | 12/2006 | Michalek et al. | 241/23 |

OTHER PUBLICATIONS

R. Wesley Farr, M.D.; Cheryl Walton, BA; Inactivation of Human Immunodeficiency Virus by a Medical Waste Disposal Process Using Chlorine Dioxide; Infection Control and Hospital Epidemiology; vol. 14 No. 9, 1993 The University of Chicago Press.

\* cited by examiner

*Primary Examiner*—Walter D Griffin
*Assistant Examiner*—Lessanework Seifu
(74) *Attorney, Agent, or Firm*—Todd E. Albanesi; Booth Albanesi Schroeder LLC

(57) ABSTRACT

An apparatus for processing medical waste is provided. The apparatus includes: (i) a drum defining a substantially cylindrical treatment chamber having a closed end and a substantially open end, wherein the drum is rotationally balanced about a rotational axis; (ii) an enclosing body supporting the drum so that the drum can be rotated within the body about the rotational axis of the drum, the body having an opening for accessing the open end of the drum, wherein the opening is located substantially in a plane perpendicular to the rotational axis of the drum; (iii) a movable barrier for selectively closing the opening for accessing the open end of the drum; (iv) a structure for supporting the enclosing body so that the pitch of the rotational axis of the drum is positioned or can be positioned in at least one position between about 0 degrees and about 30 degrees.

28 Claims, 10 Drawing Sheets

MEDICAL WASTE PROCESSOR AND PROCESSING METHOD

CROSS-REFERENCE TO RELATED APPLICATIONS

This application claims the priority of prior U.S. Application No. 60/750,170 filed Dec. 14, 2005, and having for named applicants Otley L. Smith III and R. Mason Bryant.

CROSS-REFERENCE TO RELATED APPLICATIONS

Not applicable

STATEMENT REGARDING FEDERALLY SPONSORED RESEARCH OR DEVELOPMENT

Not applicable

REFERENCE TO MICROFICHE APPENDIX

Not applicable

TECHNICAL FIELD

The invention generally relates to the field of gathering, treating, and disposing of potentially infectious medical waste.

SUMMARY OF THE INVENTION

According to a first aspect of the invention, an apparatus for treating medical waste, wherein the apparatus comprises: (i) a drum defining a substantially cylindrical treatment chamber having a closed end and a substantially open end, wherein the drum is rotationally balanced about a rotational axis; (ii) an enclosing body supporting the drum so that the drum can be rotated within the body about the rotational axis of the drum, the body having an opening for accessing the open end of the drum, wherein the opening is located substantially in a plane perpendicular to the rotational axis of the drum; (iii) a movable barrier for selectively closing the opening for accessing the open end of the drum; (iv) a structure for supporting the enclosing body so that the pitch of the rotational axis of the drum is positioned or can be positioned in at least one position between about 0 degrees and about 30 degrees; and (v) a chemical generator for generating a germicidal agent operatively connected to introduce the germicidal agent into the enclosing body According to another aspect of the invention, an apparatus for treating medical waste is provided, wherein the apparatus comprises: (i) a drum defining a substantially cylindrical treatment chamber having a closed end and a substantially open end, wherein the drum is rotationally balanced about a rotational axis; (ii) an enclosing body supporting the drum so that the drum can be rotated within the body about the rotational axis of the drum, the body having an opening for accessing the open end of the drum, wherein the opening is located substantially in a plane perpendicular to the rotational axis of the drum; (iii) a movable barrier for selectively closing the opening for accessing the open end of the drum; (iv) a structure for supporting the enclosing body so that the pitch of the rotational axis of the drum is positioned or can be positioned in at least one position between about 0 degrees and about 30 degrees; and (v) a plurality of rotationally-balanced blades positioned inside the drum, whereby when the drum is rotated, the tumbling of the medical waste in the treatment chamber onto the blades helps rupture containers and bags of the medical waste.

According to yet another aspect of the invention, a method of treating medical waste with an apparatus is provided, (A) wherein the apparatus comprises: (i) a drum defining a substantially cylindrical treatment chamber having a closed end and a substantially open end, wherein the drum is rotationally balanced about a rotational axis; (ii) an enclosing body supporting the drum so that the drum can be rotated within the body about the rotational axis of the drum, the body having an opening for accessing the open end of the drum, wherein the opening is located substantially in a plane perpendicular to the rotational axis of the drum; (iii) a movable barrier for selectively closing the opening for accessing the open end of the drum; (iv) a structure for supporting the enclosing body so that the pitch of the rotational axis of the drum is positioned or can be positioned in at least one position between about 0 degrees and about 30 degrees; and (iv) a movable mounting for the enclosing body operatively positioned between the enclosing body and the structure for supporting the enclosing body such that the pitch of the rotational axis of the drum can be selectively moved; and (B) wherein the method comprises the steps of: (i) moving the enclosing body such that the pitch of the rotational axis of the drum is between about 10 degrees and about 30 degrees and such that the opening is oriented at least partially upward to facilitate loading of medical waste at least partially downward into the treatment chamber; (ii) loading medical waste through the opening into the treatment chamber; (iii) positioning the movable barrier to close the opening; (iv) moving the enclosing body such that pitch of the rotational axis of the drum is between about 0 degrees and about 10 degrees; (v) introducing into the treatment chamber a germicidal agent; and (vi) rotating the drum to agitate the medical waste with the germicidal agent.

According to yet another aspect of the invention, a method of treating medical waste is provided comprising the steps of: (i) positioning an enclosing body for a drum such that the pitch of the rotational axis of the drum is upward such that an opening in the enclosing body for accessing the drum is oriented at least partially upward to facilitate loading of medical waste at least partially downward into the drum; (ii) loading medical waste through the opening downward into the drum; (iii) closing the opening in the enclosing body; (iv) positioning the enclosing body such that pitch of the rotational axis of the drum is substantially horizontal relative to the upward position; (v) rotating the drum to agitate the medical waste with the germicidal agent; and (vi) introducing into the enclosing body a germicidal agent to be agitated with the medical waste in the drum. Preferably, this method further comprising the steps of: (vii) re-opening the opening in the enclosing body; and (viii) positioning the enclosing body such that the pitch of the rotational axis of the drum is between about 10 and about 30 degrees and such that the opening is oriented at least partially downward to facilitate unloading of medical waste at least partially downward from the drum; and (ix) unloading the treated medical waste from the drum. More preferably, a plurality of rotationally-balanced blades are positioned inside the drum, whereby when the drum is rotated, the tumbling of the medical waste in the treatment chamber onto the blades helps rupture containers and bags of the medical waste.

According to still another aspect of the invention, a method of treating medical waste is provided comprising the steps of: (i) positioning an enclosing body for a drum such that the pitch of the rotational axis of the drum is upward such that an opening in the enclosing body for accessing the drum is oriented at least partially upward to facilitate loading of medical waste at least partially downward into the drum; (ii) loading medical waste through the opening downward into the drum; (iii) closing the opening in the enclosing body; (iv) positioning the enclosing body such that pitch of the rotational axis of the drum is substantially horizontal relative to the upward position; and (v) rotating the drum to agitate the medical waste with the germicidal agent, wherein a plurality of rotationally-balanced blades are positioned inside the drum, whereby when the drum is rotated, the tumbling of the medical waste in the treatment chamber onto the blades helps rupture containers and bags of the medical waste. Preferably, this method further includes the step of: (vi) introducing into the enclosing body a germicidal agent to be agitated with the medical waste in the drum.

It should be appreciated that the steps of the methods according to the invention can be performed in any practical sequence. It is a general object of the present invention to provide improved apparatuses and methods for treating medical waste. Other and further objects, features and advantages of the present invention will be readily apparent to those skilled in the art when the following description of the preferred embodiments is read in conjunction with the accompanying drawings.

BRIEF DESCRIPTION OF THE DRAWINGS

A more complete understanding of the present disclosure and advantages thereof may be acquired by referring to the following description taken in conjunction with the accompanying drawings, which.

DETAILED DESCRIPTION OF PRESENTLY PREFERRED EMBODIMENTS

As used herein and in the appended claims, the words "comprise," "has," and "include" and all grammatical variations thereof are each intended to have an open, non-limiting meaning that does not exclude additional elements or parts of an assembly, subassembly, or structural element.

As used herein, the term "medical waste" means and refers to any solid waste that is generated in the diagnosis, treatment, or immunization of human beings or animals, in research pertaining thereto, or in the production or testing of biologicals, including but not limited to: blood-soaked bandages; culture dishes and other glassware; discarded surgical gloves, such as after surgery; discarded surgical instruments, such as scalpels; needles, such as used to give shots or draw blood; cultures, stocks, swabs used to inoculate cultures; lancets, such as the little blades the doctor pricks a finger with to get a drop of blood; sharps containers for used needles, syringe hubs, and syringes; plastic trash bags containing such medical waste; and linen that may be infectious.

As used herein, the term "germicidal agent" means and refers to any chemical agent that is capable of significant germicidal action at standard temperature and pressure ("STP"). A chemical agent for a germicidal purpose may be formed, activated, or accelerated by the action of heat or radiation, but such heat or radiation is not otherwise required for the germicidal action by the chemical.

As used herein, the word "controller" means and refers to any mechanical, electrical, or electro-mechanical device, such as a mechanical switch or variable controller, that controls the operation of a mechanical function, for example, a motor direction, motor speed, or the opening and closing of a valve.

If there is any conflict in the usages of a word or term in this specification and one or more patent or other documents that may be incorporated herein by reference, the definitions that are consistent with this specification should be adopted.

Apparatus

Figure 1:
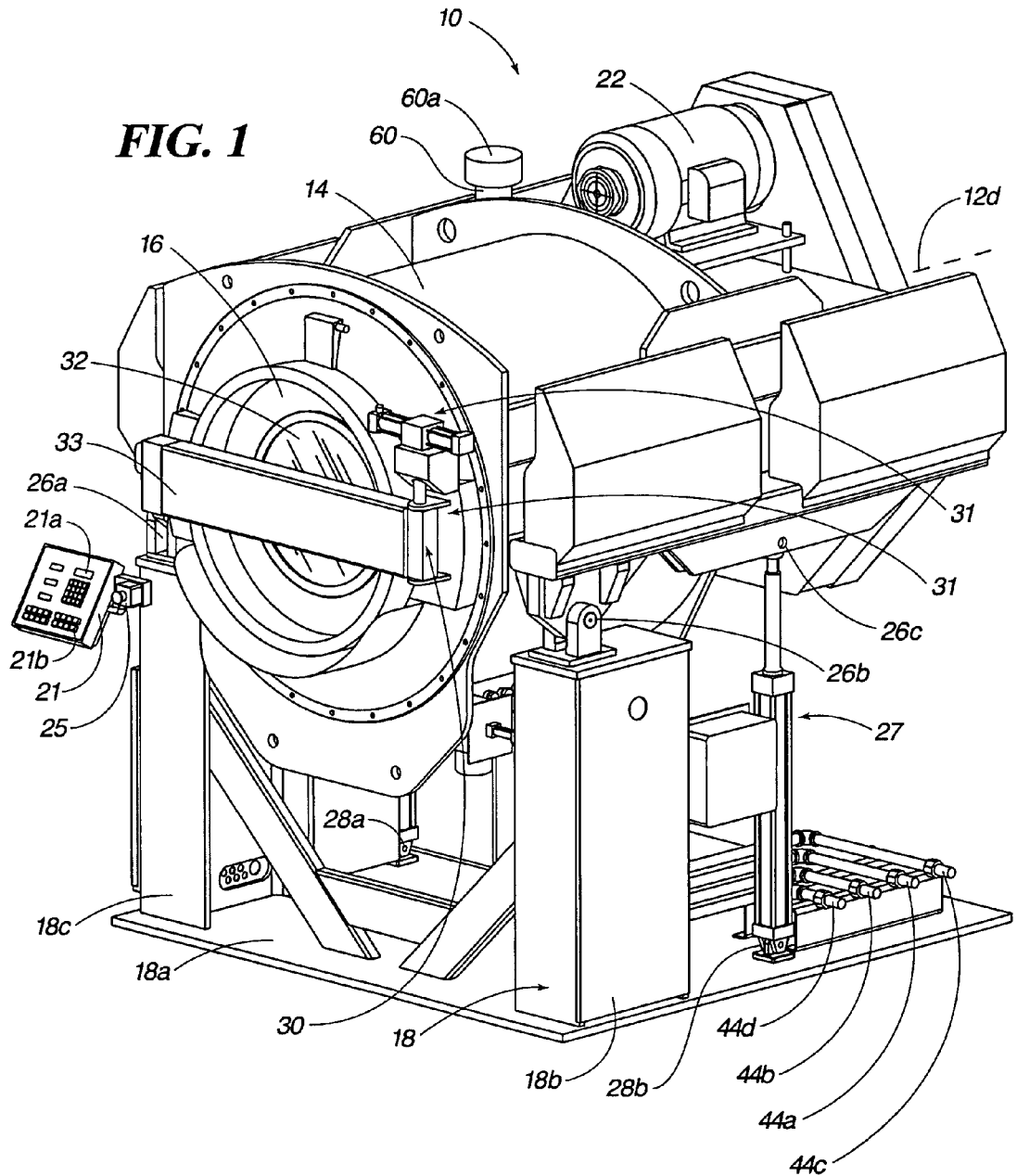
FIG. 1 is a perspective view of an apparatus according to a presently-preferred embodiment for treating medical waste, wherein the enclosing body of the apparatus (with the drum therein, not shown in this figure) is shown in a substantially horizontal position for rotating the drum and agitating medical waste in the drum and wherein the outer movable barrier is shown in a closed position.
Figure 2:
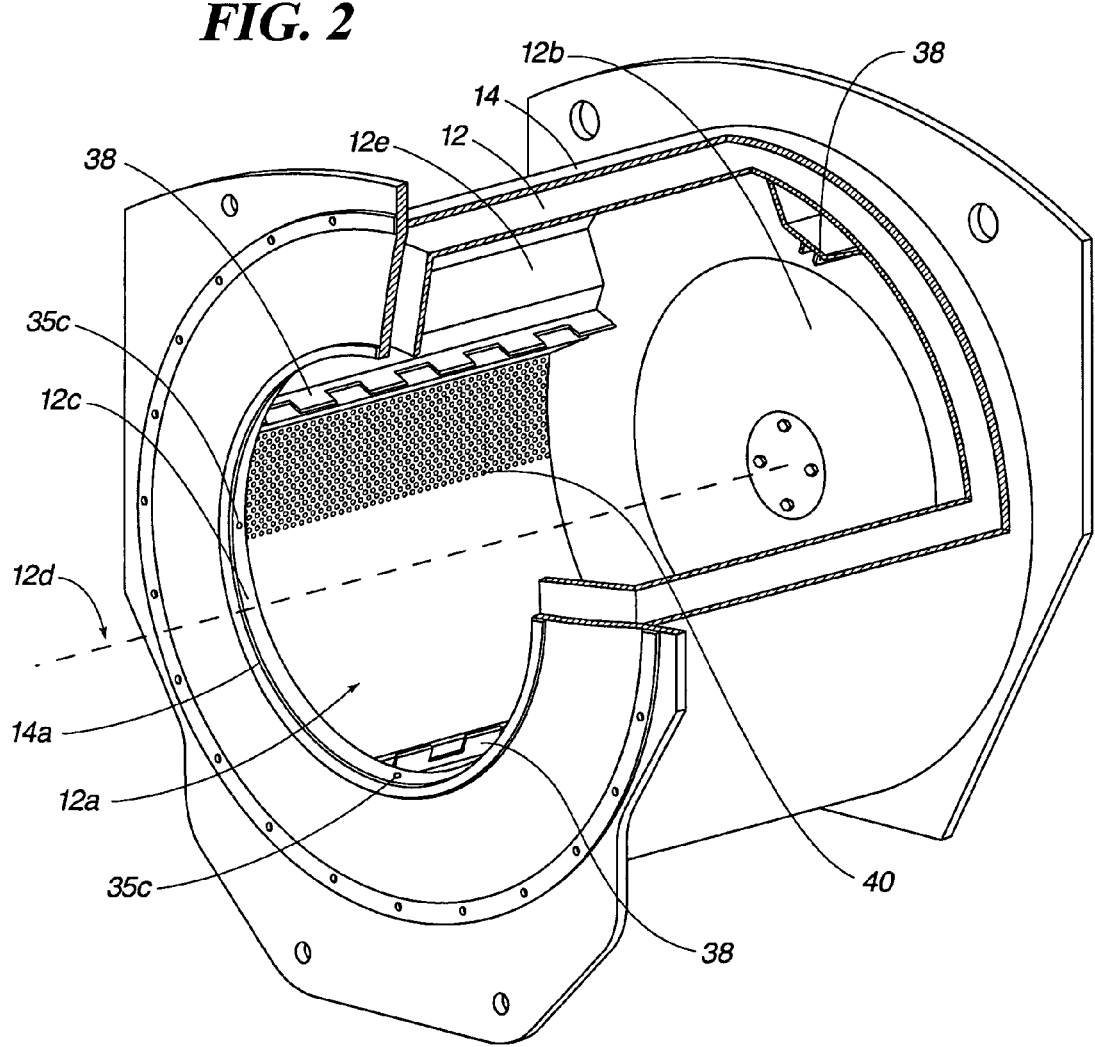
FIG. 2 is a perspective view of the inside of the enclosure body of the apparatus shown in FIG. 1 showing a cut-away into the interior processing chamber of the drum.

Referring now to FIG. 1 and FIG. 2 of the drawing, according to a first aspect of the invention, an apparatus for treating medical waste, wherein the apparatus 10 comprises: (i) a drum 12 defining a substantially cylindrical treatment chamber 12a having a closed end 12b and a substantially open end 12c, wherein the drum 12 is rotationally balanced about a rotational axis 12d; (ii) an enclosing body 14 supporting the drum 12 so that the drum can be rotated within the body 14 about the rotational axis 12d of the drum, the body 14 having an opening 14a for accessing the open end 12c of the drum, wherein the opening 14a is located substantially in a plane perpendicular to the rotational axis 12d of the drum; (iii) a movable barrier 16 for selectively closing the opening 14a for accessing the open end 12c of the drum 12; (iv) a structure 18 for supporting the enclosing body 14 so that the pitch of the rotational axis 12d of the drum is positioned or can be positioned in at least one position between about 0 degrees and about 30 degrees.

As shown in FIG. 1, the support structure 18 preferably includes a base 18a, major support legs 18a and 18b. Preferably, the apparatus 10 can support the rotational axis 12d of the drum 12 in at least a substantially horizontal position, and more preferably the apparatus 10 is adapted for pitching the axis 12a of the drum 12. upwardly and downwardly from the horizontal, as will hereinafter be described in more detail.

Also as shown in FIG. 1, the apparatus 10 has a computer control panel 21 with digital readout 21a and an input keypad 21b for controlling the apparatus 10 and processes using the apparatus 10. As will hereinafter be described in more detail, the computer control panel 21 can be used as a convenient user-interface for the various specific controllers of the apparatus and steps of the process according to the invention. As will be appreciated, the computer control panel 21 can be operatively connected to a remote computer or to the interne for remote monitoring and control of the apparatus 10 and processes using the apparatus 10.

Motor for Rotating Drum

Continuing to refer to FIG. 1, the apparatus 10 has a motor 22 operatively connected for rotating the drum 12. The motor 22 is preferably operatively positioned on the enclosing body 14. The motor 22 is preferably an electric motor. More preferably, the motor 22 is a variable speed motor.

Controller for Rotational Speed of Drum

Figure 10:
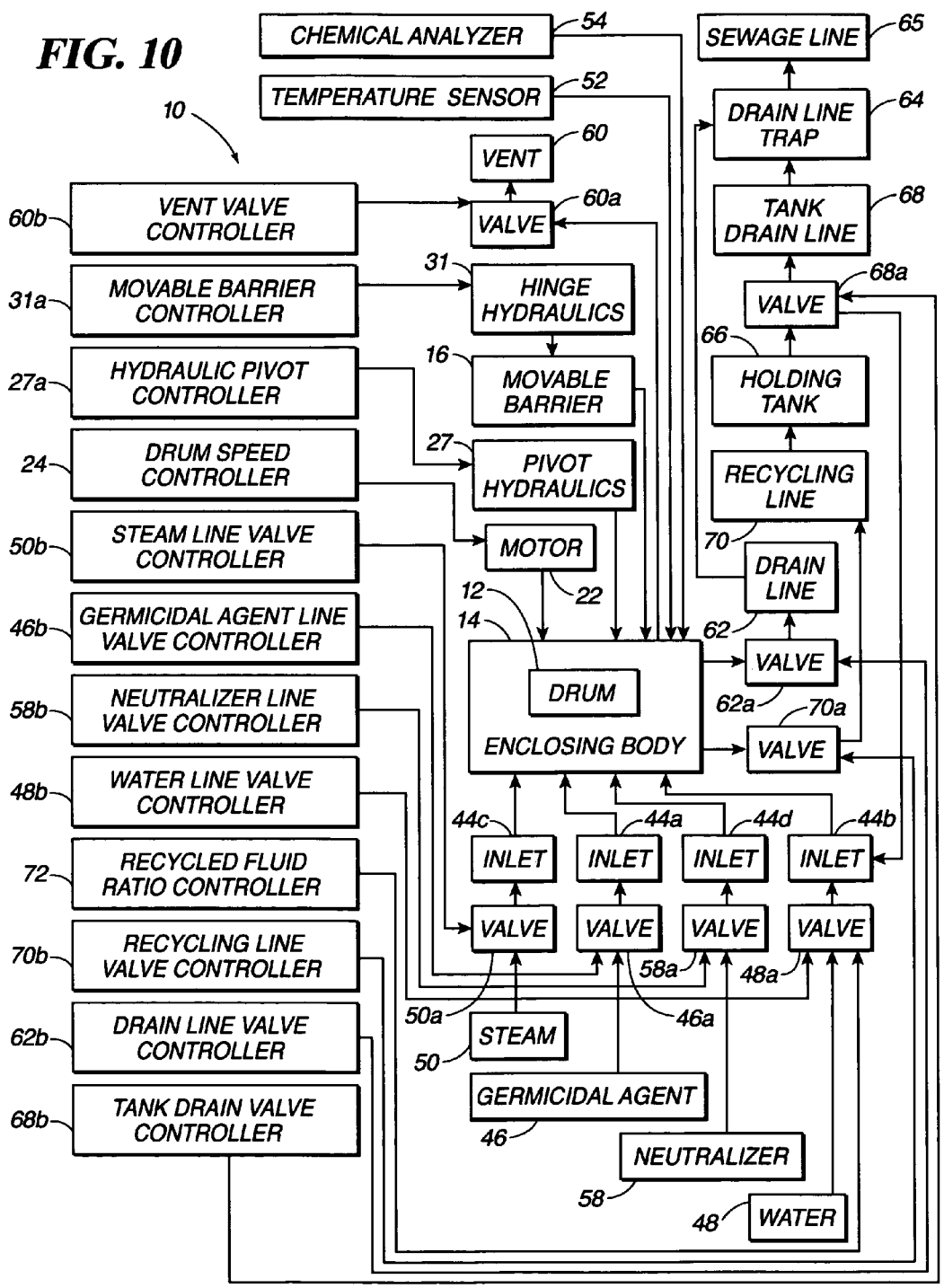
FIG. 10 is a block diagram of the components of an apparatus according to a presently-preferred embodiment.

Referring briefly to the block diagram of FIG. 10, the apparatus 10 further comprises a controller 24 for the rotational speed of the drum 12. The controller 24 is operatively connected to the motor 22. The controller 24 for the rotational speed of the drum can selectively control the rotation of the drum at a rotational speed slower than for tumbling medical waste in the drum. According to preferred embodiments, the controller 24 for the rotational speed of the drum can selectively control the rotation of the drum 12 at a rotational speed for tumbling medical waste in the drum. The controller 24 for the rotational speed of the drum can selectively control the rotation of the drum at a rotational speed for centrifugally drawing fluid from medical waste in the drum. As hereinafter described in more detail, the controller 24 is preferably part of a computer control system for the apparatus 10. The controller 24 is preferably operatively connected to and part of the computer control panel 21 shown in FIG. 1. In addition, the apparatus preferably includes an emergency stop button 25 for the motor 22 to stop the rotation of the drum if there is any major operational problem or in any kind of emergency. More preferably, the emergency stop button 25 stops all functions of the apparatus 10.

Movable Mounting for Changing Pitch to Facilitate Loading of the Drum

Referring again to FIG. 1 of the drawing, according to a presently preferred embodiment, the apparatus 10 further comprises: a movable mounting for the enclosing body 14 operatively connected between the support structure 18 and the enclosing body 14, whereby the pitch of the rotational axis 12d of the drum 12 can be selectively moved. According to a presently most preferred embodiment, the movable mounting includes at least two pivotal mountings 26a and 26b, which are preferably aligned along a common pivotal axis lying in a substantially horizontal plane. The movable mounting preferably further includes another two pivotal mountings 26c and 26d, (where 26d is not shown in FIG. 1 because it is on the other side of the apparatus 10), which are also preferably aligned along a common pivotal axis lying in a substantially horizontal plane. Preferably, at least one of the sets of pivotal mounts, either the set of pivotal mountings 26a and 26b or the set of pivotal mountings 26c and 26d, are operatively connected to hydraulic cylinders 27 for adjusting the pitch of the enclosure body 14 and drum therein. The hydraulic cylinders 27 also have pivotal mountings 28 operatively positioned between the base 18a of the support structure 18 and the hydraulic cylinders 27, which allows the hydraulic cylinders 27 to adjust their angle with the pitching of the apparatus 10.

Figure 4:
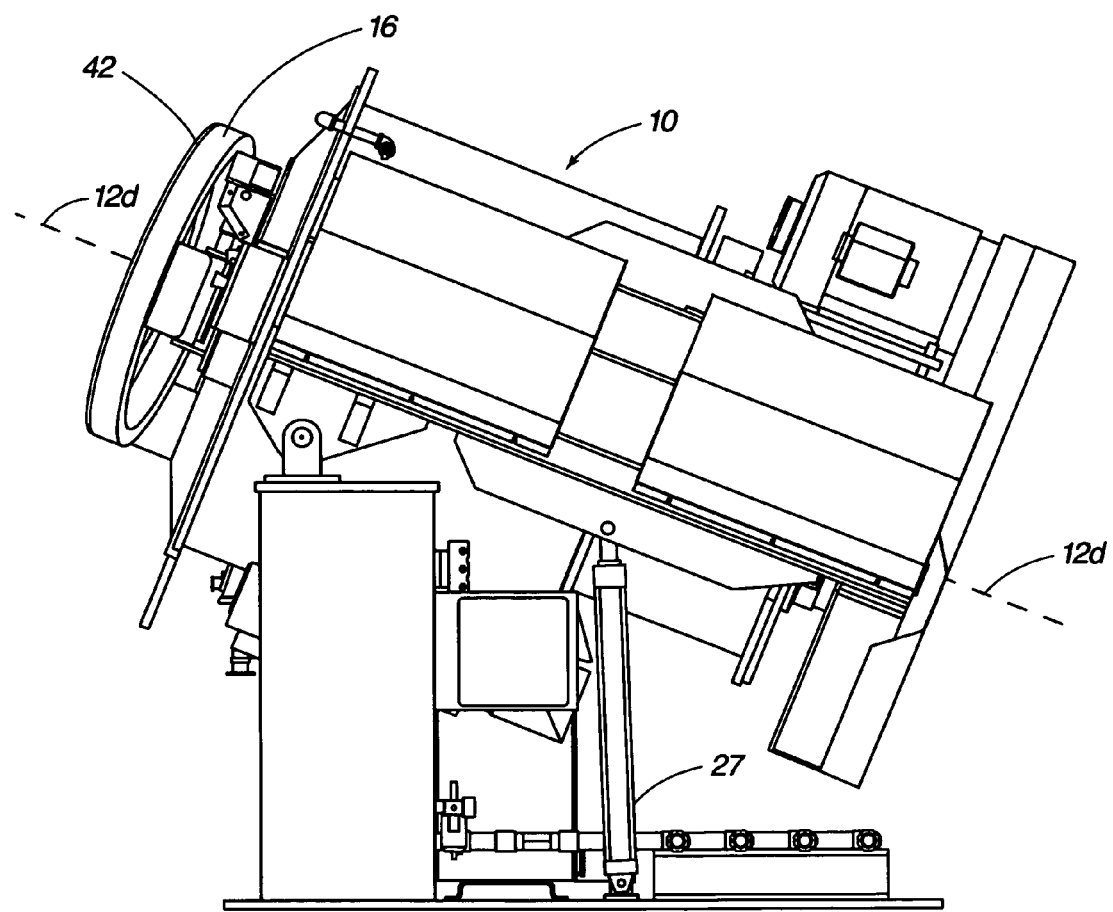
FIG. 4 is a side view of the apparatus shown in FIG. 1, wherein the enclosing body (with the drum therein, not shown in this figure) is shown in a downwardly pitched position for unloading and wherein the outer movable barrier is shown in an open position.

As shown in FIG. 4, most preferably, the movable mountings 26a and 26b and movable mountings 26c and 26d of the apparatus 10 allows the enclosing body 14 to be moved such that the pitch of the rotational axis 12d of the drum 12 is moved upward from a substantially horizontal position. Preferably, the pitch can be adjusted to be upward between about 10 degrees and about 30 degrees to the horizontal and such that the opening 14a is oriented at least partially upward to facilitate loading of medical waste at least partially downward into the treatment chamber 12a. Most preferably, the pitch can be adjusted upward to about 22 degrees to the horizontal.

Movable Mounting for Changing Pitch to Facilitate Unloading of the Drum

Figure 5:
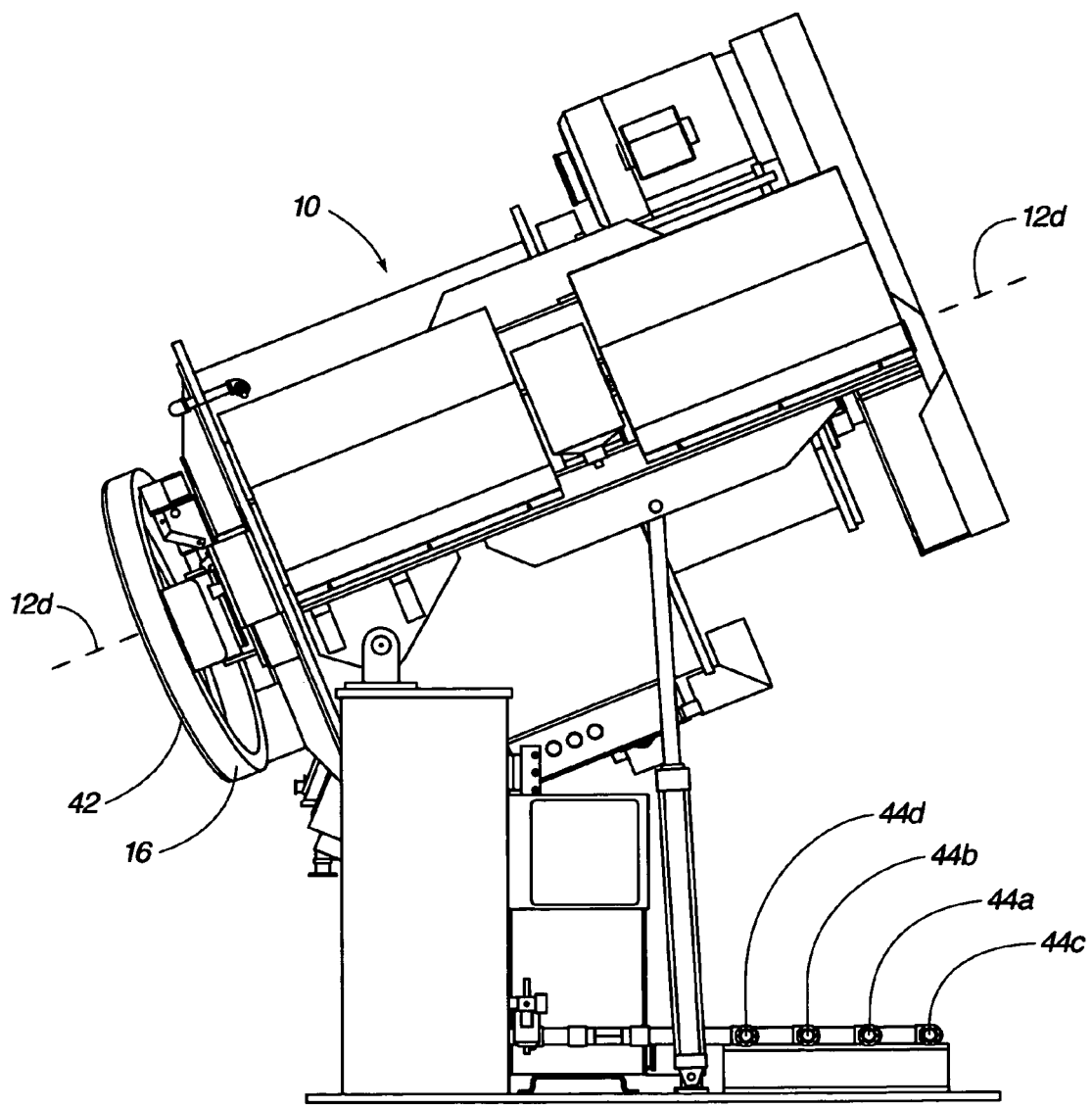
FIG. 5 is a side view of the apparatus shown in FIG. 1, wherein the enclosing body (with the drum therein, not shown in this figure) is shown in a downwardly pitched position for unloading and wherein the outer movable barrier is shown in an open position.

As shown in FIG. 5, most preferably the movable mounting 26 of the apparatus 10 allows the enclosing body 14 to be moved such that the pitch of the rotational axis 12d of the drum 12 is moved downward from a substantially horizontal position. Preferably, the pitch can be adjusted to be downward between about 10 and about 30 degrees to the horizontal and such that the opening 14a is oriented at least partially downward to facilitate unloading of medical waste at least partially downward from the treatment chamber 12a. Most preferably, the pitch can be adjusted downward to about 22 degrees to the horizontal.

As shown in FIGS. 1, 4, and 5, the pitch of the rotational axis 12d of the drum 12 in the enclosing apparatus 14 is preferably moved by hydraulic cylinders 27. As previously described in more detail, the hydraulic cylinders 27 are preferably operatively connected between the enclosing body 14 and the support structure 18. Referring briefly to FIG. 10, a controller 27a for the hydraulic system 27 is operatively connected to the hydraulic system 27. As hereinafter described in more detail, the controller 27a is preferably part of a computer control system for the apparatus 10. The controller 27a is preferably operatively connected to and part of the computer control panel 21 shown in FIG. 1.

Controller for Slow Rotation of Drum for Loading/Unloading

Referring again to the block diagram of FIG. 10, according to a preferred embodiment of the invention, the controller 24 is capable of controlling a very slow rotational speed of the drum 12. The controller 24 is operatively connected to the motor 22. The controller 24 for preferably can selectively control the rotation of the drum for less than a single rotation of the drum, whereby such rotation can facilitate loading or unloading of the drum 12. Most preferably, the controller 24 for very slow rotational speed of the drum 12 provides for selectively rotating the drum in either rotational direction. Most preferably, the controller 24 for very slow rotational speed of the drum provides for variable rotational speed. Further, most preferably, the controller 24 for very slow rotational speed of the drum 12 comprises a manual controller. A purpose of such very slow rotation and rotation for less than a single rotation of the drum 12 is to allow for the automated loading or unloading of the medical waste, with minimal risk of injury to a human operator of the apparatus 10. As hereinafter described in more detail, the controller 24 is preferably part of a computer control system for the apparatus. The controller 24 is preferably operatively connected to and part of the computer control panel 21 shown in FIG. 1.

Outer Movable Barrier

Referring to FIG. 1, preferably, the outer movable barrier 16 is a door having hinges 30. This allows for easy opening and closing of the opening 14a of the enclosing body 14.

The movable barrier 16 is preferably moved on the hinges 30 by a hydraulic system 31. The hydraulic system 31 is preferably operatively connected between the enclosing body 14 and the movable barrier 16. Referring briefly to FIG. 10, a controller 31a for the hydraulic system 31 is operatively connected to the hydraulic system 31. As hereinafter described in more detail, the controller 31a is preferably part of a computer control system for the apparatus 10. The controller 31a is preferably operatively connected to and part of the computer control panel 21 shown in FIG. 1.

Figure 6:
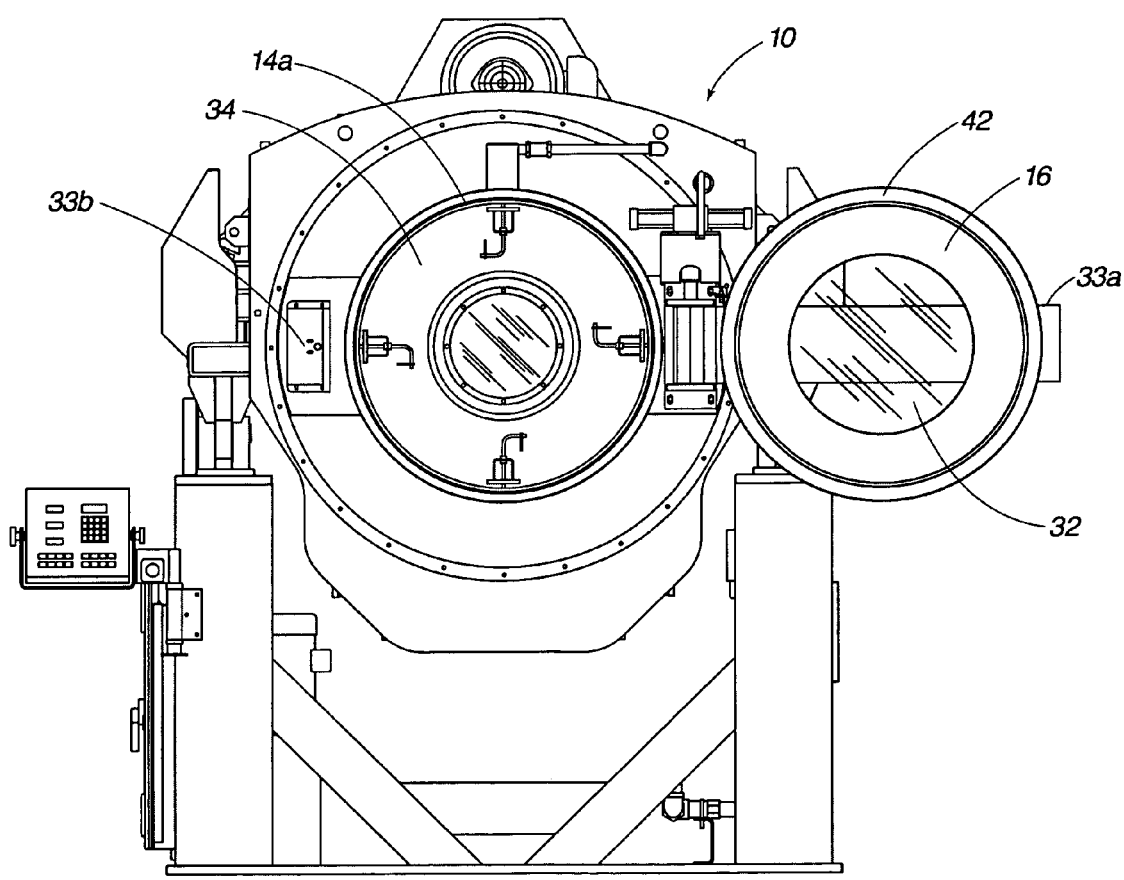
FIG. 6 is a front view of the apparatus shown in FIG. 1, wherein the enclosing body (with the drum therein, not shown in this figure) is shown in a substantially horizontal position with an inner movable barrier shown positioned to close the drum inside the enclosing body.

The movable barrier 16 also preferably includes a latch system 33 for latching the movable barrier 16 shut. Referring to FIG. 6, the latch system 33 can include, for example, a latching arm 33a and a receiving body 33b. More preferably, the latch 33 is hydraulically operated, which hydraulic operation can be part of the hydraulic system 31 for the operation of the movable barrier 16.

Continuing to refer to FIG. 1, preferably, the movable barrier 16 further comprises a transparent window 32 for viewing inside the enclosure body toward the treatment chamber 12a when the movable barrier 16 is in a closed position for the opening 14a.

Inner Movable Barrier for Drum

Figure 7:
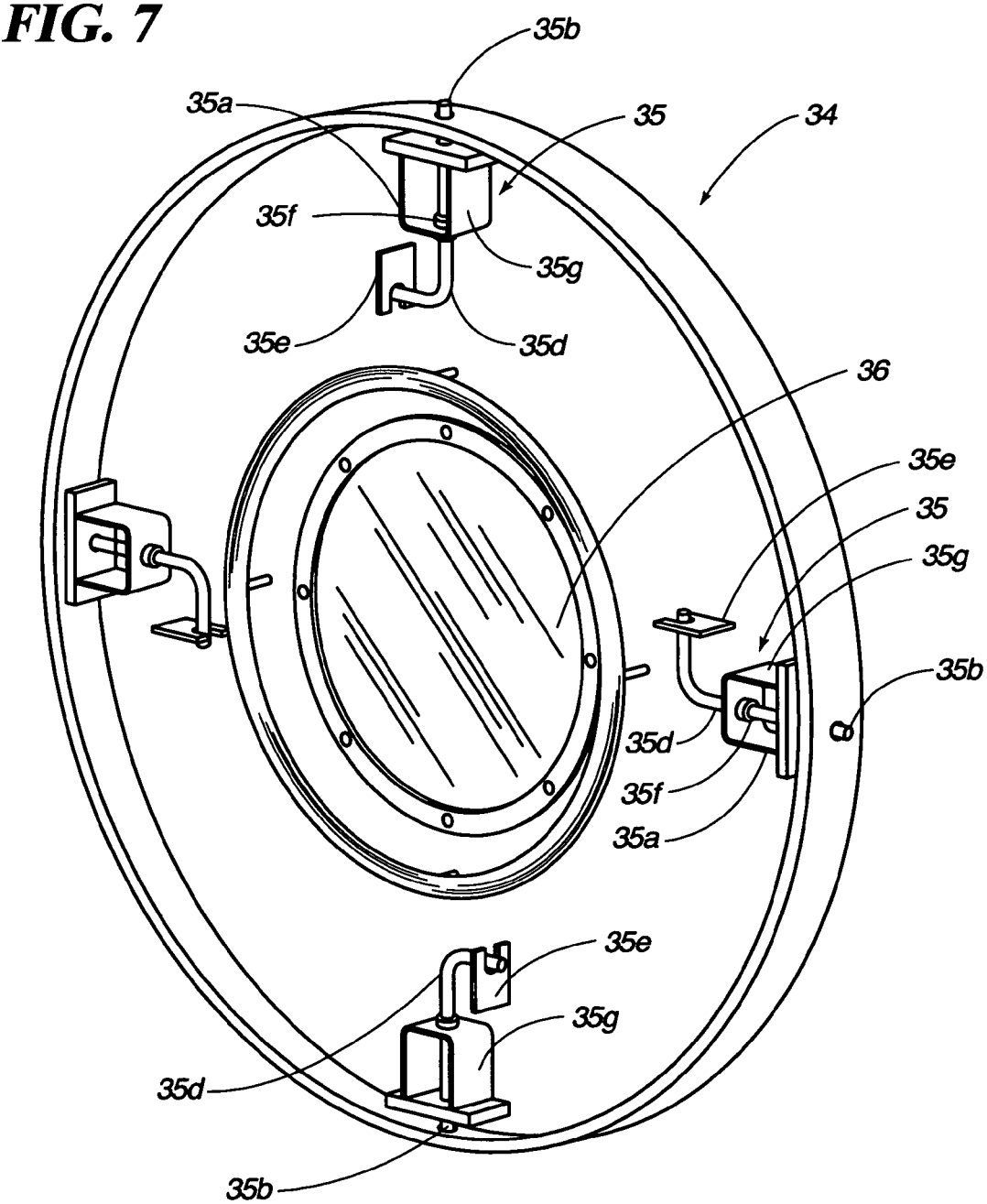
FIG. 7 is a detail of a presently-preferred embodiment of the inner movable barrier shown in FIG. 6, including four latches for attaching the inner movable barrier to the drum (not shown in this figure).

Referring now to FIGS. 6 and 7, the apparatus 10 preferably further comprises: an inner movable barrier 34 for selectively closing the open end 12c of the drum 12, thereby preventing any substantial solids of medical waste from escaping from the treatment chamber 12a during rotation of the drum into enclosing body 14 outside drum 12.

According to a presently most preferred embodiment of the invention, the inner movable barrier 34 for the drum 12 comprises a latching system 35 for selectively attaching the inner movable barrier 34 to the drum. For example, the latching system 35 can comprise a plurality of latch assemblies 35a, adjacent the periphery 34a of the inner movable barrier 34, wherein each of the latches 35a has a pin 35b, and a corresponding plurality of apertures 35c (shown in FIG. 2) in the periphery of the open end 12c of the drum 12. Thus, the inner movable barrier 34 can be positioned adjacent the open end 12c of the drum and the pins 35b can be moved into latching engagements with the plurality of apertures 35c in the periphery of the open end 12c of the drum. The inner barrier 34 can be removed from the open end 12c of the drum by pulling the pins 35b out of engagement with the plurality of apertures 35c. Each of the pins 35b preferably includes a locking end 35d that can be locked into a cradle 35e and biased into the locked cradle with a spring 35f in a pin holding body 35g attached to the inner movable barrier.

Most preferably, the inner movable barrier 34 further comprises an inner transparent window 36 for viewing inside of the treatment chamber 12a of the drum.

Blades in Drum

Figure 3:
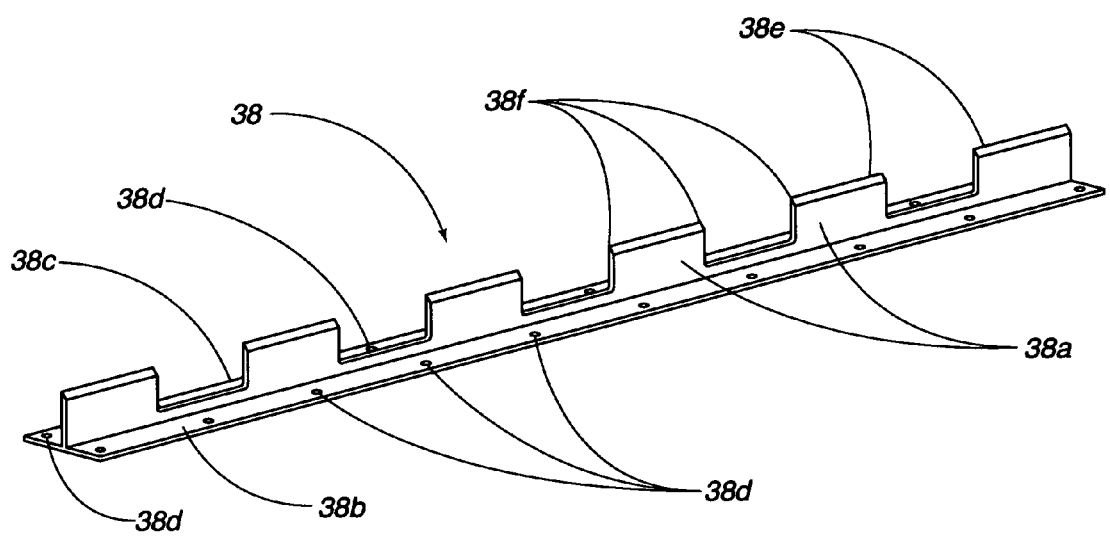
FIG. 3 is a perspective view of a presently-preferred embodiment of a blade for the interior of the drum.

Referring now to FIGS. 2 and 3 of the drawing, the apparatus 10 preferably comprises: a plurality of rotationally-balanced blades 38 positioned inside the drum 12, whereby when the drum is rotated, the tumbling of the medical waste in the treatment chamber 12a onto the blades 38 ruptures containers and bags of the medical waste. Preferably, the blades 38 are positioned on an inside wall of the drum 12. Preferably, the blades 38 are adapted to rupture disposal containers for needles or syringes that may be present in the medical waste when the drum 12 rotates at a speed to tumble the medical waste in the treatment chamber 12a. The preferred arrangement of the blades is a segmented design to insure that all the waste material is broken open to allow both the liquid and/or gas to penetrate all parts of the waste load to facilitate the kill. The blades 38 are preferably positioned along the entire length of the drum 12. If desired, additional blades (not shown) can be placed adjacent the closed end of the drum to provide additional rupturing, penetration, and breaking of the medical waste as it is tumbled in the drum. This can be especially helpful, for example, if the drum is pitched backward a few degrees during tumbling of the medical waste when agitating it with a germicidal agent, which reduces the amount of the medical waste tumbling against the movable barrier 16.

FIG. 3 in particular illustrates a preferred embodiment of a blade 38 for use in the invention. The blade 38 preferably is formed of stainless steel or similarly strong material that is also resistant to chemical corrosion. The blade 38 is preferably in the form of an elongated body having a blade portion 38a and flange portions 38b and 38c. The flange portions 38b and 38c preferably have a plurality of apertures 38d therein. The apertures in the flange portions of the blade 38 can be used for removably securing the blade 38 to the interior body of the drum or a support structure 12e of the drum 12, as shown in FIG. 2.

Continuing to refer to FIG. 3, the blade portion 38a preferably has substantially sharpened edges 38e. Further, the blade portion 38a is preferably segmented, which provides additional sharp corner edges 38f. The sharp corner edges 38f are believed to be particularly helpful in rupturing items commonly present in medical waste.

Drum Holes in Drum

Referring again to FIG. 2, preferably, at least a portion of the drum 12 has a plurality of drum holes 40 adapted to allow the passage of fluid while retaining solid medical waste material therein. More preferably, the size and shape of the drum holes 40 in the drum 12 are adapted to prevent passage of whole needles and hubs of the sizes and types that are most commonly in medical waste. For example, preferable the drum holes 40 are circular and the diameter of each of the drum holes 40 is less than or equal to 0.25 inches.

Fluid-Tight Enclosing Body

Referring to FIG. 6, according to a further aspect of the invention, the enclosing body 14 is fluid-tight, the movable barrier 16 is fluid-tight, and the apparatus 10 further comprises: a fluid-tight seal 42 operatively positioned between the enclosing body 14 and the removable barrier 16, whereby the enclosing body 14 is fluid tight when the movable barrier 16 closes the opening 14a for accessing the open end 12c of the drum 12. More preferably, when the removable barrier 16 closes the opening 14a of the enclosing body 14 (and any other inlets, vents, drain lines, or other ports in the enclosing body 14 are also closed) the enclosing body 14 is fluid tight up to at least 25 pounds per square inch ("psi") above standard atmospheric pressure. More preferably, the enclosing body 14 is fluid tight up to about 100 psi above standard atmospheric pressure. Preferably, all the materials, seals, and valves, etc. of the apparatus that are expected to be routinely exposed to the germicidal agent during operation of the apparatus 10 are selected to be resistant to chemical corrosion. For example, most preferably, the fluid-tight seal 42 is a Viton® material, which is highly resistant to chemical corrosion.

Fluid Inlet

Referring again to FIGS. 1 and 10, in the preferred example of the apparatus 10 having a fluid-tight enclosing body 14, the apparatus 10 further comprises: at least one fluid inlet for delivering a treatment fluid into the enclosing body. It is to be understood, of course, that the apparatus 10 can have a single fluid inlet or that the function or functions of the fluid inlet can be served by a plurality of fluid inlets, such as fluid inlets 44a, 44b, 44c, and 44d, as hereinafter described in more detail, which can be plumbed in a variety of configurations. Preferably, the apparatus 10 further comprises: at least one fluid inlet valve, as hereinafter described in more detail, so that the fluid inlet or inlets 44a-d can be selectively opened or closed, whereby the treatment fluid can be selectively introduced into the enclosing body 14. In addition, the apparatus 10 preferably further comprises: at least one controller, as hereinafter described in more detail, for the fluid inlet valve or valves. As hereinafter described in more detail, the controller is preferably part of a computer control system for the apparatus.

Fluid Inlet to Germicidal-Agent Source

Referring to FIG. 10, according to a preferred embodiment, the fluid inlet 44*a* is adapted to be connected to a germicidal-agent source 46, whereby the treatment fluid can comprise the germicidal agent. The germicidal-agent source 46 can be a supply tank (not shown) for the germicidal agent. Preferably, the apparatus includes a germicidal agent line valve 46*a* to the inlet 44*a* so that the germicidal-agent source 46 to the fluid inlet 44*a* can be selectively opened or closed. The apparatus 10 also preferably further comprises: a controller 46*b* for the germicidal agent line valve. As hereinafter described in more detail, the controller 46*b* is preferably part of a computer control system for the apparatus. The controller 46*b* is preferably operatively connected to and part of the computer control panel 21 shown in FIG. 1.

Germicidal Agent Generator

Continuing to refer to FIG. 10, more preferably than a supply tank for germicidal agent, however, the germicidal agent 46 source of the apparatus 10 comprises: a chemical generator for generating the germicidal agent, wherein the chemical generator is operatively connected to the controller for introducing the germicidal agent. Most preferably, the chemical generator is a chlorine dioxide generator and the germicidal agent is chlorine dioxide.

Fluid Inlet to Water Source

Preferably, the fluid inlet 44*b* is adapted to be connected to a water source 48, whereby the treatment fluid can optionally comprise water. The water source can be connected to a city water supply, for example. Preferably, the apparatus 10 includes a water line valve 48*a* to the fluid inlet 44*b* so that the water source 48 to the fluid inlet 44*b* can be selectively opened or closed. The apparatus 10 also preferably further comprises: a controller 48*b* for the germicidal agent line valve. As hereinafter described in more detail, the controller 48*b* is preferably part of a computer control system for the apparatus. The controller 48*b* is preferably operatively connected to and part of the computer control panel 21 shown in FIG. 1.

Fluid Inlet to Superheated Water or Steam Source

Preferably, the fluid inlet 44*c* is adapted to be connected to a superheated water or steam source 50, whereby the treatment fluid can optionally comprise superheated water or steam. Preferably, the apparatus 10 includes a steam line valve 50*a* to the fluid inlet 44*c* so that the steam source 50 to the fluid inlet 44*c* can be selectively opened or closed. The apparatus 10 also preferably further comprises: a controller 50*b* for the steam line valve 50*a*. More preferably, the controller 50*b* introduces at least sufficient superheated water or steam from the steam source 50 into the treatment chamber 12*a* to substantially increase the temperature within the treatment chamber, whereby the sufficient time to achieve "Level IV Microbial Inactivation" is substantially shortened relative to ambient temperature. As hereinafter described in more detail, the controller 50*b* is preferably part of a computer control system for the apparatus. The controller 50*b* is preferably operatively connected to and part of the computer control panel 21 shown in FIG. 1.

Steam Generator

Preferably, the apparatus 10 further comprises: a steam generator for the steam source 50.

Temperature Sensor

Continuing to refer to FIG. 10, the apparatus 10 preferably further comprises: a temperature sensor 52 operatively connected for determining the temperature of a treatment fluid inside the treatment chamber 12*a*. The temperature sensor 52 can be operatively connected to a temperature readout visible to the operator of the apparatus 10, and more preferably to a computer control system for the apparatus 10, which is hereinafter described in more detail. The temperature sensor 52 is preferably operatively connected to the computer control panel 21 shown in FIG. 1. For example, the temperature readout can be part of the information that can be displayed in the digital readout 21*a*.

Chemical Analyzer for Germicidal Agent

Continuing to refer to FIG. 10, preferably the apparatus 10 further comprises: a chemical analyzer 54 for the germicidal agent operatively connected to the controller for the introduction of the germicidal agent into the treatment chamber. Preferably, the chemical analyzer 54 is connected for determining the germicidal agent concentration of a treatment fluid in the treatment chamber 12*a*, either by direct sampling from the treatment chamber or by indirect sampling of the treatment fluid drawn from the treatment chamber. The chemical analyzer 54 can be operatively connected to determine the concentration of a source of treatment fluid or a portion of a fluid used for the treatment fluid, for example, the germicidal-agent source 46 or a recycled treatment fluid that may have some germicidal agent concentration remaining therein. With the data from the chemical analyzer, the controller for the introduction of the germicidal agent into the treatment chamber can balance the streams, for example, from the germicidal-agent source 46 and a water source 48, superheated water or steam source 50, or a recycled treatment fluid source (as hereinafter described in more detail), to achieve a desired concentration of the germicidal agent in a treatment fluid introduced into the treatment chamber 12*a*. As hereinafter described in more detail, the controller is preferably part of a computer control system for the apparatus. The chemical analyzer 54 is preferably operatively connected to the computer control panel 21 shown in FIG. 1.

Neutralizing Agent Source

Continuing to refer to FIG. 10, the apparatus 10 preferably further comprises: a controller for introducing a neutralizing agent for the germicidal agent into the treatment chamber 12*a*. The fluid inlet 44*d* is adapted to be connected to a neutralizing agent source 58 for neutralizing the germicidal agent, whereby the germicidal agent can optionally be at least partially neutralized prior to discharge of the germicidal agent from the treatment chamber 12*a*. The apparatus 10 further comprises: a neutralizer line valve 58*a* to the fluid inlet 44*d* so that the neutralizing agent source 58 to the fluid inlet 44*d* can be selectively opened or closed. In addition, the apparatus 10 further comprises: a controller 58*b* for the neutralizing line valve. As hereinafter described in more detail, the controller 58*b* is preferably part of a computer control system for the apparatus. The controller 58*b* is preferably adapted for adjusting the amount or concentration of neutralizing agent to accomplish the desired degree of neutralization of the germicidal agent expected to be or measured to be in the treatment chamber of the apparatus.

Vent and Scrubber

The apparatus 10 preferably further comprises: a vent 60 to the atmosphere. The apparatus further comprises: a valve 60*a* for the vent 60, whereby the enclosing body 14 can be selectively vented or prevented from venting to the atmosphere. In this embodiment, the apparatus 10 preferably further comprises: a controller 60*b* for the valve 60*a* for the vent 60. As hereinafter described in more detail, the controller 60*b* is preferably part of a computer control system for the apparatus. The controller 60*b* is preferably operatively connected to and part of the computer control panel 21 shown in FIG. 1.

A scrubber (not shown) operatively in line with the vent 60 is preferably added which utilizes the neutralization solution for a bubble through process to neutralize any fugitive gas, and a HEPA filter will top off the scrubber to further reduce any possible release to atmosphere of the treated or untreated aerosols. The neutralization solution will be refreshed with each load, as it will be used to neutralize the active solution in the normal batch process. The scrubber acts to neutralize any fugitive gas emissions, and the HEPA filter removes any organic aerosols that should be released from the drum. A switch is activated by the controller that calls for the neutralization solution to be added.

Drain Line

Preferably, the apparatus 10 further comprises: a drain line 62 from the enclosing body 14 for draining liquid from the enclosing body. It is to be understood, of course, that the apparatus 10 can have a single drain line 62 or that the function or functions of the drain line 62 can be served by a plurality of drain lines, which can be plumbed in a variety of configurations. The apparatus 10 further comprises: a drain valve 62a for the drain line 62, whereby the liquid can be selectively contained or drained from the enclosing body 14. The apparatus further comprises: a controller 62b for the drain valve 62a. As hereinafter described in more detail, the controller 62b is preferably part of a computer control system for the apparatus. The controller 62b is preferably operatively connected to and part of the computer control panel 21 shown in FIG. 1.

Trap in Drain Line

Figure 8:
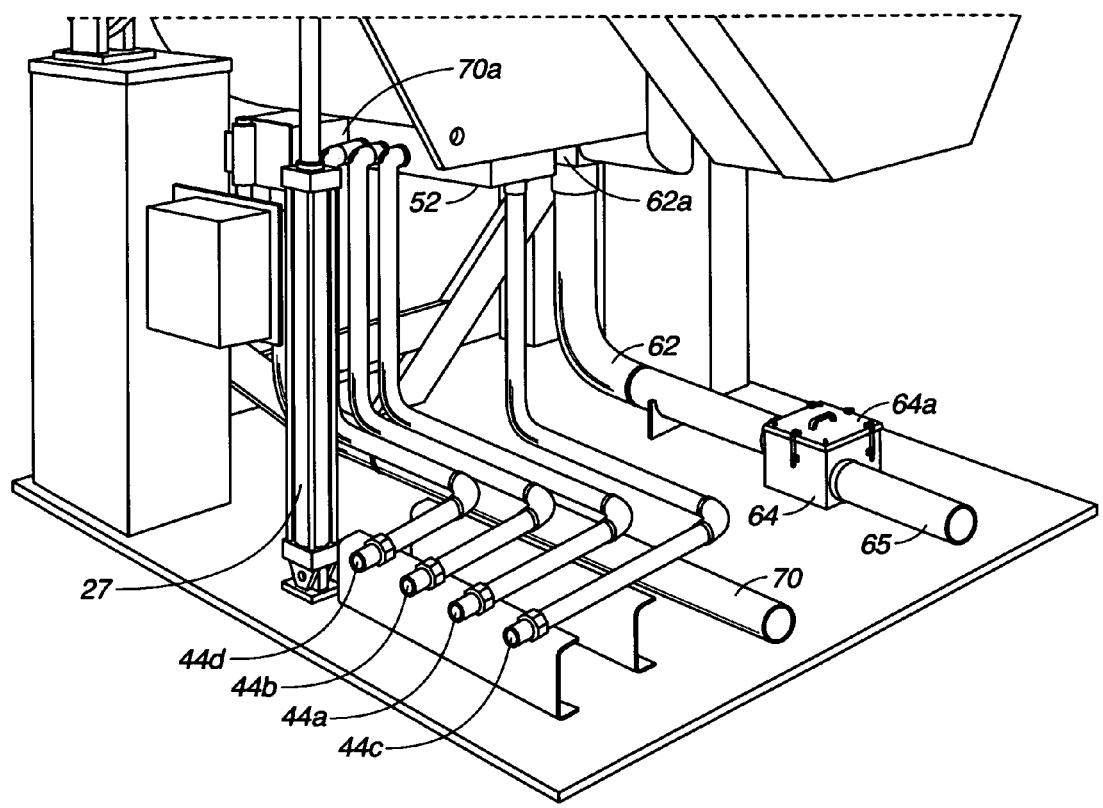
FIG. 8 is a detail of a lower, rear of a portion of the apparatus showing a plurality of fluid inlets and a drain line with a trap therein.

Referring to FIG. 8, the apparatus 10 preferably further comprises: a trap 64 in the drain line 62 for any needles and other debris from the medical waste that may escape the treatment chamber 12a, whereby such debris is prevented from escaping downstream of the trap 64, for example, into a sewage line 65 to sewage disposal.

Figure 9:
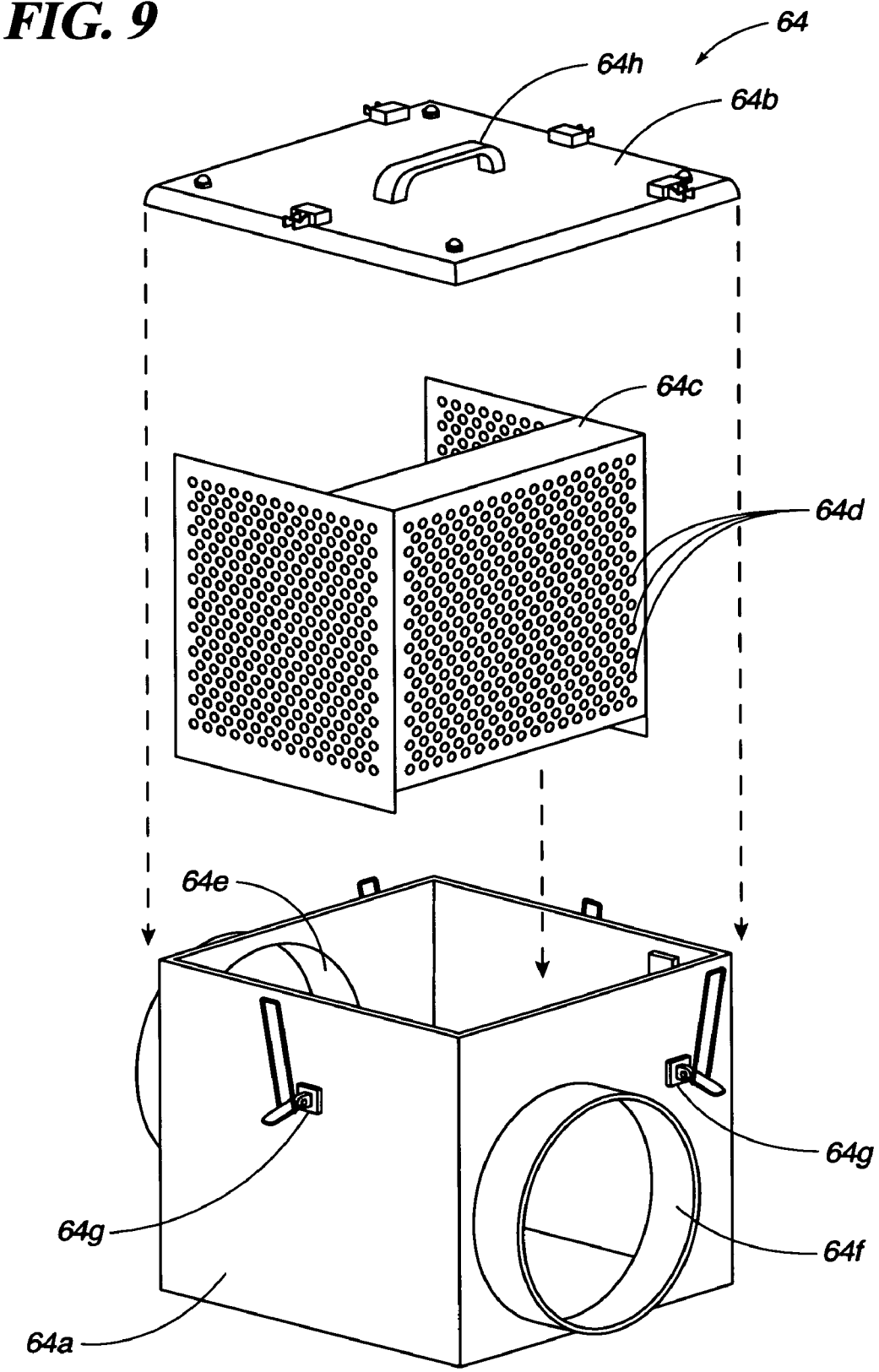
FIG. 9 is an exploded view of a trap with basket for the drain line of the apparatus according to a presently-preferred embodiment.

Referring now to FIG. 9, the trap 64 in the drain line 62 preferably further comprises a trap body portion 64a and a removable cover 64b for accessing a removable basket 64c positioned in the trap body portion 64a, the basket having drain holes 64d, whereby the basket 64c can be manually removed from the trap body portion 64a to remove or dump the solid contents in the basket 64b. The size and shape of the drain holes 64d in the removable basket 64c are adapted to prevent passage of smaller sizes of medical waste than the drain holes 40 in the drum 12.

The trap body 64a is adapted to be operatively connected to the drain line 62 with a trap inlet 64e. The trap body 64a is adapted to be operatively connected to a sewage line 65 with a trap outlet 64f.

The trap body preferably has lid latches 64g for keeping the lid closed on the trap body. The lid preferably includes a trap handle 64h.

Liquid Holding Tank

Referring to FIG. 10, according to a preferred embodiment, the apparatus 10 further comprises: a liquid holding tank 66 operatively connected to the drain line 62 from the enclosing body 14. Preferably, the liquid holding tank 66 is fluid-tight, which helps control the escape of germicidal agent or other fumes into the surrounding atmosphere.

Recycling Line for Liquid Holding Tank

For the liquid holding tank 66 for spent treatment fluid, the apparatus 10 further comprises: a tank drain line 68 from the holding tank 66 for draining liquid in the holding tank to sewage disposal, and a recycling line 70 from the holding tank 66 for directing liquid in the holding tank into the enclosing body 14. The apparatus further comprises: a tank drain valve 68a for the tank drain line 68 and a recycling line valve 70a for the recycling line 70, whereby liquid can be selectively contained or drained from the holding tank 66 through the tank drain line 68, and preferably through the drain line trap 64 to the sewage line 65 for sewage disposal or selectively directed into the enclosing body 14. The apparatus further comprises: a controller 68b for the tank drain valve; and a controller 70b for the recycling line valve. As hereinafter described in more detail, each of the controllers 68b and 70b is preferably part of a computer control system for the apparatus. The controllers 68b and 70b are preferably operatively connected to and part of the computer control panel 21 shown in FIG. 1.

Chemical Analyzer for Germicidal Agent from Recycling Line

Again referring to FIG. 10, for an apparatus 10 connected to or comprising a liquid holding tank 66 for used treatment fluid, the apparatus preferably further comprises: a chemical analyzer, most preferably chemical analyzer 54, for determining the concentration of the germicidal agent in a liquid from the holding tank. It is to be understood, of course, that the chemical analyzer 54 can be operatively connected to sample fluids from various sources or that a plurality of chemical analyzers can be employed, for example, a single analyzer for each source desired to be analyzed for germicidal agent or other chemical property. The apparatus 10 preferably further comprises: a controller 72 for the ratio of fluids from the holding tank 66 and the germicidal-agent source 46 to achieve a desired concentration of germicidal agent for use as a treatment fluid to be introduced into the treatment chamber 12a. As hereinafter described in more detail, the controller 72 is preferably part of a computer control system for the apparatus. The controller 72 is preferably operatively connected to and part of the computer control panel 21 shown in FIG. 1.

Computer Control

The apparatus 10 preferably further comprises: a computer control system 74 for at least the controller for the introduction of germicidal agent. Most preferably, the computer control system is operatively connected to be the central controller for all the selectively operable elements of the apparatus 10. Preferably, the computer controller is operatively connected to a plurality of sensors on the apparatus for detecting the relevant operating state of the apparatus for each controller that is selectively operable. Preferably, the computer control system is operatively connected to the Internet for remote access and communication with the computer controller.

Method of Treating Medical Waste

According to yet another aspect of the invention, a method of treating medical waste with an apparatus is provided, (A) wherein the apparatus comprises: (i) a drum 12 defining a substantially cylindrical treatment chamber 12a having a closed end 12b and a substantially open end 12c, wherein the drum 12 is rotationally balanced about a rotational axis 12d; (ii) an enclosing body 14 supporting the drum 12 so that the drum can be rotated within the body 14 about the rotational axis 12d of the drum, the body 14 having an opening 14a for accessing the open end 12c of the drum 12, wherein the opening 14a is located substantially in a plane perpendicular to the rotational axis 12a of the drum; (iii) a movable barrier 16 for selectively closing the opening 14a for accessing the open end 12c of the drum 12; (iv) a structure 18 for supporting the enclosing body 14 so that the pitch of the rotational axis 12a of the drum 12 is positioned or can be positioned in at least one position between about 0 degrees and about 30 degrees; and (iv) a movable mounting 26 for the enclosing body 14 operatively positioned between the enclosing body 14 and the structure 18 for supporting the enclosing body 14 such that the pitch of the rotational axis 12d of the drum 12 can be selectively moved; and (B) wherein the method comprises the steps of: (i) moving the enclosing body 14 such that the pitch of the rotational axis 12*d* of the drum is between about 10 degrees and about 30 degrees and such that the opening 14*a* is oriented at least partially upward to facilitate loading of medical waste at least partially downward into the treatment chamber 12*a*; (ii) loading medical waste through the opening 14*a* into the treatment chamber 12*a*; (iii) positioning the movable barrier 16 to close the opening 14*a*; (iv) moving the enclosing body 14 such that pitch of the rotational axis 12*d* of the drum is between about 0 degrees and about 30 degrees; (v) introducing into the treatment chamber 12*a* a germicidal agent; and (vi) rotating the drum 12 to agitate the medical waste with the germicidal agent.

Moving Body on Movable Mounting to Change Pitch for Loading

The step of loading medical waste into the treatment chamber 12*a* preferably further comprises: pouring the medical waste from a bin (not shown) through the upwardly oriented opening 14*a* for accessing the open end 12*c* of the drum 12 and into the treatment chamber 12*a*. The step of loading preferably further comprises: rotating the drum 12 about the rotational axis 12*d* of the drum so that the treated medical waste is rotated upward on an inner wall of the drum 12 and then tumbles by gravity farther down into the treatment chamber 12*a* of the drum. The step of loading preferably further comprises: rotating the drum 12 at least one-half of a revolution about the rotational axis 12*d* in one rotational direction and rotating the drum at least one-half a revolution about the rotational axis 12*d* in the opposite rotational direction.

The step of moving the enclosing body 14 such that the pitch of the rotational axis 12*d* of the drum 12 is between about 0 degrees and about 30 degrees further comprises: moving the enclosing body 14 such that the pitch of the rotational axis 12*d* of the drum 12 is substantially 0 degrees to a horizontal plane. It is believed that this position provides maximum benefit of tumbling the medical waste with the germicidal agent in the treatment chamber 12*a*. However, as discussed above, it is expected that it can be helpful to tumble the medical waste in the drum when the rotational axis 12*d* of the drum 12 is pitched slightly upward (backward) a few degrees from the horizontal, which helps keep the medical waste tumbling slightly toward the rear, closed end of the drum 12*b*. For example, it is presently believed that the rotational axis 12*d* of the drum 12 can be advantageously positioned at about 5 degrees from the horizontal plane with the front, open end 12*c* of the drum oriented slightly upward.

Moving the Movable Mounting to Change Pitch for Unloading

The method preferably further comprises the steps of: (vii) moving the movable barrier 16 to reopen the opening 14*a*; and (viii) moving the enclosing body 14 such that the pitch of the rotational axis 12*d* of the drum 12 is between about 10 and about 30 degrees and such that the opening 14*a* is oriented at least partially downward to facilitate unloading of medical waste at least partially downward from the treatment chamber 12*a*; and (ix) unloading the treated medical waste from the treatment chamber 12*a*. Preferably, the step of unloading further comprises: rotating the drum 12 about the rotational axis 12*d* of the drum so that the treated medical waste is rotated upward on an inner wall of the drum 12 and then tumbles by gravity out of the open end 12*c* of the treatment chamber 12*a* of the drum and to the outside of a lower edge of the opening 14*a* in the enclosing body 14. Preferably, the step of unloading further comprises: rotating the drum 12 at least one-half of a revolution about the rotational axis 12*d* in one rotational direction and rotating the drum at least one-half a revolution about the rotational axis in the opposite rotational direction.

Collecting Medical Waste & Disposing of Disinfected Medical Waste

The method preferably further comprises the step of: collecting the medical waste into a bin for transport to the apparatus 10. The method preferably also further comprises the step of: unloading the medical waste that has been treated in the apparatus 10 into a bin for transport to a non-medical waste collection area for disposal as non-medical waste.

Method with Blades Positioned in Drum

Preferably, the apparatus 10 employed in the method further comprises: a plurality of rotationally-balanced blades 38 positioned inside the drum 12, whereby during the step of rotating the drum to agitate the medical waste with the germicidal agent, the tumbling of the medical waste in the treatment chamber 12*a* onto the blades 38 ruptures containers and bags of the medical waste. This helps expose the interiors of such containers and bags to the germicidal agent. Preferably, the blades 38 are positioned on an inside wall of the drum 12. Preferably, the blades 38 are adapted to rupture disposal containers for needles or syringes that may be present in the medical waste when the drum 12 rotates at a speed to tumble the medical waste in the treatment chamber 12*a*.

Fluid-Tight Enclosing Body for Apparatus in Method

Preferably, the enclosing body 14 of the apparatus 10 employed in the method is fluid-tight, the movable barrier 16 is fluid-tight, and the apparatus further comprises: a fluid-tight seal 42 operatively positioned between the enclosing body 14 and the removable barrier 16, whereby the enclosing body 14 is fluid tight when the movable barrier 16 closes the opening 14*a* for accessing the open end 12*c* of the drum 12.

Closing Vent while Germicidal Agent is in Treatment Chamber

In a preferred embodiment wherein the enclosing body 14 is fluid tight, the apparatus 10 employed in the method preferably further comprises: a vent 60 to the atmosphere. The apparatus further comprises: a valve 60*a* for the vent 60, whereby the enclosing body 14 can be selectively vented or prevented from venting to the atmosphere. In this embodiment, the apparatus 10 preferably further comprises: a controller 60*b* for the valve 60*a* for the vent 60. In a preferred embodiment of the method with such a preferred embodiment of the apparatus 10, the vent 60 is closed while germicidal agent is introduced into the treatment chamber 12*a*.

Introducing Germicidal Agent

The step of introducing into the treatment chamber 12*a* a germicidal agent preferably further comprises the step of: introducing a germicidal agent having at least a sufficient effectiveness in at least a sufficient concentration under conditions at least sufficient to achieve "Log 6 Kill." According to the presently most-preferred embodiment, the germicidal agent comprises chlorine dioxide.

Heating—e.g., with Superheated Water or Steam

The method preferably further comprises the step of heating the medical waste in the treatment chamber. The step of heating the medical waste can further comprise, for example: introducing superheated water or steam into the treatment chamber 12*a*.

Neutralizing Agent for Germicidal Agent

The method preferably further comprising the step of: after the step of agitating the medical waste with the germicidal agent in the treatment chamber 12*a*; neutralizing any residual germicidal agent. Where the germicidal agent comprises chlorine dioxide, the neutralizing agent comprises a sulfite.

More preferably, the neutralizing agent comprises a water-soluble inorganic sulfite salt, such as sodium or potassium sulfite.

Recycling Germicidal Agent

According to a presently preferred embodiment, the method further comprises the step of: recycling the germicidal agent for use in a subsequent treatment of another batch of medical waste.

Example Machine and Method

A medical waste processor and processing method has been designed and developed as an on-site alternative for healthcare facilities by Oncore Technologies, LLC located in Grand Prairie, Tex. The processor and method is designed for use by any hospital facility or consortium of area healthcare facilities.

The processor and method treat infectious medical waste by subjecting such waste to a liquid germicidal solution in a liquid-tight chamber. Steam may also be used to activate or accelerate the process. The chamber is mechanically moved or rotated to create a turbulence that mechanically agitates the infectious waste with the germicide solution.

Preferably, the movement or rotation of the chamber macerates the infectious medical wastes using cutting blades mounted on the interior of the rotating chamber. More preferably but not necessarily, the cutting blades are positioned to be in opposing relation to help more effectively macerate the infection medical wastes. The blades are adapted to rupture bags and containers of medical waste or that are typically included in medical waste.

After mechanically agitating the infectious medical waste with the liquid germicidal solution in the chamber under sufficient conditions of concentration of the germicidal agent or agents in the liquid germicidal solution, possibly using steam or heat to accelerate the germicidal action, mechanical agitation, and agitation time necessary for germicidal contact to convert the infection medical waste into a noninfectious waste, the Unit neutralizes or inactivates the germicidal solution.

In addition, the processor and method preferably includes separating the liquids from the solid waste materials to convert infectious medical waste into a noninfectious waste. Preferably, the liquids are separated from the solid waste materials after the liquid germicidal solution has been neutralized or inactivated.

An example of such a medical waste processor, which is also capable of being used in the medical waste processing method, is based on a washing apparatus that has been modified for the purposes of this invention, including with the addition of (1) a germicidal solution generator, (2) opposing cutting blades in the chamber, and (3) a controller that regulates germicidal addition and all cycle processes. An example of a suitable washing apparatus for use in the present invention is the FLPS-1200 Tilt End-Loading Apparatus, which is commercially available from Washex, Inc. In this example, the "Unit" has a capacity of processing approximately 275 of medical waste per cycle. At approximately 20 minutes per cycle, it has a capacity of approximately 500-750 pounds per hour. A larger Unit is currently capable of treating approximately 450 pounds per cycle. Future models will have the capacity to treat from 100 to 500 pounds per cycle. A smaller waste-volume processing model is envisioned for the future to meet the needs of the smaller hospital or large clinic.

The Unit most preferably utilizes chlorine dioxide to inactivate microbial organisms. The Unit successfully inactivates challenge microorganisms representing vegetative bacteria (Staphyloccus aureus), viruses (attenuated Poliovirus 2), fungi (Candida albicans), protozoa (Giardia cysts), Mycobacteria (M. bovis), and bacterial endospores (B. stearothermophilus).

Level of Treatment

As summarized in Table I, treatment efficacy studies conducted on the Unit utilized bacterial spores from Bacillus stearothermophilus. It is well established that in the hierarchy of microbial resistance, bacterial endospores exhibit the greatest degree of resistance to both heat and chemical biocides than do vegetative bacteria, viruses, fungi, and protozoa. This difference in degree of resistance is often orders of magnitude with variables dependent on the organism and the chemical or thermal agent to which the organism is subjected. Four microbial inactivation levels have been defined by both State and Territorial Association on Alternate Treatment Technologies ($STA^2T^2$) in the Technical Assistance Manual: State Regulatory Oversight of Medical Waste Treatment Technologies (1999) and in Guidance for Evaluating Medical Waste Treatment Technologies (USEPA, 1993). Both these documents define Level IV Microbial Inactivation as having the ability to inactivate $10^6$ bacterial spores. Although B. subtilis spores are typically used as the chemical resistance standard, spores from B. stearothermophilus provide an equivalent measure of resistance to chemical inactivation and either is recommended to verify Level IV microbial inactivation. In this study B. stearothermophilus spores were used to demonstrate microbial effectiveness of the Unit. Use of B. stearothermophilus spores is required in performing these tests on the Unit since the spores are thermophilic and require temperatures of 55-61° C. to germinate to a vegetative state. Incubation at these temperatures precludes the growth of common contaminants that might be introduced to the spore strips during the neutralization cycle that follows the chlorine dioxide treatment cycle.

TABLE I

Summary of Treatment Efficacy

| Microorganism | Log Reduction Achieved (Test Average) | Log Reduction Required |
|---|---|---|
| B. stearothermophilus spores | 6.6* | 6.0 |

*Limited by the initial spore concentration on the spore strips

Characterization of the Proposed Treatment Process

The Unit is a chemical inactivation medical waste treatment technology utilizing chlorine dioxide to inactivate microorganisms. Combined physical turbulent agitation and internal cutting blades provide the mechanisms to break open closed sharps containers and to saturate medical wastes with chlorine dioxide solution during the treatment process. Through a pre-programmed controller, the unit sequences to automatically:

1) Load medical waste into the treatment chamber;
2) Close and seal the door to the treatment chamber;
3) Generate chlorine dioxide solution to the proper concentration;
4) Fill the chamber with the prescribed concentration and amount of chlorine dioxide solution, and steam, if desired to accelerate the treatment process;
5) Initiate and complete the processing cycle;
6) Initiate and complete a chlorine dioxide neutralization cycle;
7) Discharge neutralized processing solution; and
8) Open the treatment chamber door and automatically discharge treated medical waste residue.

Waste Compatibility with Proposed Treatment Process

Medical waste treatment efficacy studies were conducted using a composite simulated medical waste stream that was comprised, by weight, of: The simulated load was comprised, by weight, of: 5% organic material (protein supplement), 27% cellulose, 31% non-woven plastics, 7% liquids, and 11% hard plastics. Previously decontaminated (steam sterilized) sharps containers (19%) were also placed into the waste stream to determine the efficiency of their physical treatment by the process. The protein supplement was added to simulate a five percent bovine blood content that would typify the organic load in a medical waste stream originating from blood, body fluids, diagnostic tissue samples, and laboratory cultures and growth support mediums. The plastic and cellulose simulated waste components representative of medical waste items consisted of woven plastics (e.g., drape and gown materials), hard plastics (e.g., materials made of polyethylene, polypropylene, or polystyrene), and cellulose (e.g., paper towels, cotton chucks, etc.). No attempt was made in the studies conducted to ascertain the effectiveness of the Unit against singular high-organic waste streams such as animal carcasses, their body parts, bulk whole blood, and animal bedding. It is known that chlorine dioxide reacts with organic material to deplete the initial chlorine dioxide concentration as a result of that interaction. From the data collected evaluating residual chlorine dioxide concentration in the effluent after treating the waste (before neutralization), the organic load never exceeded the lowering of the initial concentration of chlorine dioxide by more than 15% under 5% organic load conditions.

It is known that chlorine dioxide is only affected by organic materials and that the addition of organic material (primarily the protein supplement) was the only challenge that the waste load composition presented. Plastics, glass, and metals have no affect on the microbial inactivation effectiveness of chlorine dioxide. Since this system adds a liquid (the germicide solution), liquids also present no limitation to the technology.

Density and compaction of the waste stream also present no limitation since the unit provides a high degree of turbulent agitation during treatment. In combination with the cutting blades and turbulent water forces that are generated during waste processing, even closed and sealed sharps containers are broken open and contents scattered.

The amount of organic materials in the medical waste stream has the potential to influence the chlorine dioxide concentration in the treatment solution. As previously noted, the Unit has been designed and demonstrated to effectively treat a composite medical waste stream consisting of bulk blood, blood products, body fluids, microbiological wastes, sharps waste, and isolation wastes. Primary waste loads of high organic-containing wastes from animals including bedding and carcasses have not been tested to determine treatment conditions required to meet treatment efficacy criteria. This system is designed to flood the waste with chlorine dioxide solution, and steam, if desired, agitating it to allow total waste contact and allow for dilution and complete treatment of typical concentrations (tested at 5% w/w) of organic materials such as bulk blood, blood products, and laboratory cultures. Under these conditions, residual chlorine dioxide levels exceed 300 ppm after treatment.

The turbulent forces of the treatment process present no physical limitation to the types of medical waste that can be treated by the unit unlike the damage that can occur to shredders or hammermills by a small stainless steel object. The interior of the unit is constructed of materials that can withstand the impact of hard, dense objects. No mechanical breakdown or compromise of the treatment process is foreseen.

Although chemicals are not considered part of a medical waste load, small amounts may somehow enter the waste stream. No incompatibilities with small trace amounts of the typical chemicals (i.e., alcohols, formaldehyde, glutaraldehyde) that might be associated with medical wastes are envisioned. No mechanical breakdown or compromise of the treatment process is foreseen.

Microbiological Testing Procedures

Efficacy tests were conducted with *B. stearothermophilus* spores (indicator strips containing in excess of 6 $Log_{10}$ of spores) to demonstrate microbial effectiveness of the Unit. Spores strips were removed from their protective envelopes, wrapped in a nylon material, placed into perforated screw-capped polypropylene tubes, and attached to the inside of the treatment chamber of the Unit prior to waste loading. Upon completion of the treatment cycle and neutralization cycles, the tubes were removed from the unit for off-site quantitative/qualitative analysis. The method of introduction of the spores to the treatment process was chosen to both retrieve intact spore strips yet subject them to the same physical conditions that waste would receive during the process.

Note that *B. stearothermophilus* is now referred to as *Geobacillus stearothermophilus*. For the purposes of this discussion, *B. stearothermophilus* will be the terminology used in this report.

By-Products and Discharges of the Treatment Process

As with any medical waste treatment methodology that employs chemical process to treat medical waste, certain by-products are expected to be generated from that process. For the Unit, these bi-products include potential bioaerosols, gaseous chlorine dioxide, chlorine dioxide treatment solution, and waste residue. To control and mitigate these bi-products to protect from occupational exposures or environmental releases, every effort has been taken to "engineer out" these potential exposures or releases during both routine and unscheduled operations through the incorporation of monitoring and control devices throughout Unit. These monitoring and control devices are summarized below.

Biological Aerosols

The Unit has been designed as a batch-process system that minimizes or precludes bio-aerosols from forming or being released prior to or during processing. Medical waste is placed directly into the treatment chamber via an automated tipper or manually and once the chamber is filled, the hydraulic door is automatically closed and sealed for operation. The waste remains intact as the chamber is filled to the proper amount and concentration of the chlorine dioxide solution and once filled, the chamber initiates its rotational sequence to create turbulent conditions that subject the entire content of the waste load to the biocide. During the process some pressure is created releasing small concentrations and amounts of any volatilized chlorine dioxide to the chamber's venting system. An activated carbon filter may be entrained in the ventilation duct to trap any fugitive emissions. The vented chlorine dioxide inactivates bio-aerosols that might escape via this route. Any chlorine dioxide that may escape to the atmosphere will be quickly inactivated by sunlight.

Liquid Treatment Solution

No residual chlorine dioxide will be discharged to the sanitary sewer system, although chlorite will be formed as from the waste-chlorine dioxide interaction. The Unit utilizes a chlorine dioxide solution that is applied to the waste to provide microbial inactivation. During treatment chlorite ions are formed as chlorine dioxide is used up in disinfection reactions. Upon completion of the treatment process, any remaining chlorine dioxide is neutralized using either a sodium or potassium sulfite solution to form either sodium or potassium sulfite. Using sodium sulfite as the neutralizing agent example, the reaction proceeds as follows: $5Na_2SO_3 + 2ClO_2 + H_2O \rightarrow 5Na_2SO_4 + 2HCl$. Chlorite will react with the neutralization agent, although somewhat more slowly, but as the wastewater mixes with other water and the pH is reduced, the reaction will speed up. In addition, the presence of sulfides in the municipal sewer system will rapidly consume any chlorite that remains.

Chemical Emissions

The Unit utilizes chlorine dioxide to inactivate infectious agents that might be present in medical wastes. Chlorine dioxide is generated via a chlorine dioxide generator developed and patented by Dr. Greg D. Simpson. U.S. Pat. No. 6,171,558 issued Jan. 9, 2001 to Greg D. Simpson is hereby incorporated by reference in its entirety. This generator can use either the precursors of (1) chlorine gas and aqueous sodium chlorite or (2) sodium hypochlorite, hydrochloric acid, and sodium chlorite.

Chlorine dioxide is a strong oxidizer and as such, may cause irritation to the skin and redness and irritation to the eyes. Chlorine dioxide is harmful if inhaled with an assigned Permissible Exposure Level Time Weighted Average of 0.1 ppm and Threshold Limit Value TWA of 0.1 ppm. The Unit has been designed to prevent operator exposure to chlorine dioxide through a self-contained process in which chlorine dioxide solution is generated, applied to the waste, neutralized, and discharged to the sanitary sewer. The treatment chamber is watertight during operation. During the process some pressure is created releasing small concentrations and amounts of any volatilized chlorine dioxide to the chamber's venting system. An activated carbon filter may be entrained in the ventilation duct to trap any fugitive emissions.

The Unit has been designed with both automatic and manual shutdown modes that are or can be activated in the event of a malfunction or emergency event to preclude the release of chemical agents. The unit has been additionally designed to be self-contained so that in the event of a malfunction or unplanned event, no or negligible chemical releases to the environment will occur.

Odors

A deodorization system (HEPA filter) may be used to deodorize any vapors or gasses that may be emitted from the unit via the unit's ventilation system. Any chlorine dioxide that may be released to the atmosphere will have a very limited lifespan since it decomposes within minutes in the presence of sunlight. Processed waste will contain no chlorine dioxide (the only source of odor in this system) since the chlorine dioxide is neutralized prior to the waste's automatic removal from the Unit. The waste material itself will be deodorized by the normal action of the chlorine dioxide, which is a deodorizer.

Treated Waste Residue

The Unit generates a waste residue that is comprised of macerated waste materials that are microbiologically inert after treatment. The waste will retain some moisture from the chlorine dioxide treatment/neutralizing solutions. However, the amount of liquid/moisture retained is minimal since the treated waste is subjected to dewatering via a high velocity spin cycle at the end of the neutralization cycle. Preferably, the spin cycle generates centrifugal forces sufficient to remove most of the liquid in the residual waste. For example, the Unit is designed to provide a spin cycle that generates centrifugal forces of up to about 300 g. Chlorine dioxide in the waste will be neutralized prior to waste discharge. The treated waste residue would be deemed non-infectious and would be classified as a general solid waste acceptable for landfill disposal.

Environmental Effects of the Treatment Process

The Unit medical waste treatment processor utilizes high water turbulence and internal cutting blades to break open waste containers and expose the waste to chlorine dioxide solution to inactivate microorganisms. Prior to discharge of the chlorine dioxide solution and the treated waste, remaining chlorine dioxide is "neutralized" with either sodium or potassium sulfite resulting in no discharge of chlorine dioxide to the sanitary sewer or to the landfill. The chemical reaction (sodium sulfite) is as follows: $5Na_2SO_3+2ClO_2+H_2O \rightarrow 5Na_2SO_4+2HCl$. During treatment chlorite ions are formed as chlorine dioxide is used up in disinfection reactions. Chlorite will react with the neutralization agent, although somewhat more slowly, but as the wastewater mixes with other water and the pH is reduced, the reaction will speed up. In addition, the presence of sulfides in the municipal sewer system will rapidly consume any chlorite that remains. No negative effects are anticipated on the environment from the use or disposal of treated waste from the Unit. The treatment solution and treated medical waste is neutralized prior to its discharge from the unit resulting in no negative chemical discharges to the sewer or landfill.

The Unit has been designed with both automatic and manual shut-down modes that are or can be activated in the event of a malfunction, emergency or unplanned event to preclude the release of chemical or biological agents. The unit has been additionally designed to be self-contained so that in the event of a malfunction or unplanned event, no or negligible chemical or biological releases to the environment would occur.

The Unit generates a waste residue that is comprised of ruptured and macerated materials that are microbiologically inert after treatment. The waste will retain minor amounts of moisture from the neutralized chlorine dioxide treatment solution. The amount of moisture will be minimal due to the dewatering affect of the high-speed final spin cycle that generates in excess of 300 g to the waste load. The treated waste residue would be deemed non-infectious and would be classified as a general solid waste acceptable for landfill disposal. The waste residue will be disposed as a general solid waste in a solid waste landfill. There are no by-products identified as a hazardous waste as a result of this treatment process.

Occupational Hazards

As with any medical waste treatment methodology that employs a chemical treatment process to treat medical waste, potential occupational hazards can exist in the operation of such a unit and with the handling of medical waste destined for treatment in the unit. As such, potential exposures to occupational hazards may include exposures to electrical, mechanical/physical, chemical, and biological sources associated with the operation of the Unit. Every effort has been taken to "engineer out" these potential exposures during both routine and unscheduled operations. Additionally, the use of personal protective equipment is also prescribed and integrated with appropriate training where and when necessitated.

The Unit was designed with safety being of foremost concern. Every possible effort has been made to incorporate features into the system that guard against potential electrical, mechanical, chemical, and biological hazards. The unit has also been equipped with a series of protective devices, termed "interlocks", which have been designed to additionally protect personnel when internal maintenance or repair is performed. The safety features incorporated into the Unit are summarized below.

Electrical

As with any high voltage equipment like the Unit, there are inherent electrical dangers that must be recognized by all personnel operating and maintaining/repairing the unit. Primary in electrical safety is the institution and implementation of "Lockout-Tagout" procedures. These procedures and related design characteristics of the unit have been developed to purposely disable the unit when personnel might be at increased risk of injury due to internal repair, maintenance, troubleshooting or when accessing the "Master Control Center."

During waste processing, there is an "Emergency Master Switch" that will de-energize every sub-system of the Unit. The emergency master switch is located on the Master Control Board. The emergency switch is designed for life threatening situations only. All wiring and switches on the unit are enclosed and meet UL standards. Any activities involving any electrical circuitry are only to be performed by a competent electrician knowledgeable of the unit's electrical circuitry.

Mechanical

The Unit has been designed to limit exposure to any moving parts. Moving parts on the Unit include the hydraulic door, hydraulic lift for the treatment chamber, the optional hydraulic tipper, and the treatment chamber's belt drive. During the any hydraulic lift operation, the closing of the door and the activation of the chamber lift, both audible and visible alarms are activated to alert the operator and others of the potential danger for the movement of these parts. The treatment chamber's belt drive is completely enclosed and cannot be accessed during the unit's operation.

Chemical

The Unit utilizes chlorine dioxide to inactivate infectious agents that might be present in medical wastes. Chlorine dioxide is generated via a chlorine dioxide generator developed and patented by Dr. Greg D. Simpson. This generator can use either the precursors of (1) chlorine gas and aqueous sodium chlorite or (2) sodium hypochlorite, hydrochloric acid, and sodium chlorite. The system is totally enclosed. As the chlorine dioxide generator operates and fills the unit based on vacuum eduction, any leaks in tubing or other components will result in air induction, and not the leaking of precursors. No contact of personnel with chlorine dioxide or its precursors will occur at any time during the process. The creation and use of the chlorine dioxide will be automatic, as will the neutralization step at the end of the process. Procedures have been developed for the storage of all chemicals required for the generation of chlorine dioxide and its neutralization. The process can be activated or accelerated by the use of heat, for example, in the form of superheated water or steam. Although this is not required for treatment, it is expected it would be useful to speed up the process time or if additional treatment is required for particular types of infectious material.

Biological

The Unit has been designed as a batch-process system that minimizes or precludes bio-aerosols from forming or being released prior to or during processing. Medical waste is placed directly into the treatment chamber via an automated tipper or manually and once the chamber is filled, the hydraulic door is automatically closed and sealed for operation. The waste remains intact as the chamber is filled to the proper amount and concentration of the chlorine dioxide solution and once filled, the chamber initiates its rotational sequence to create turbulent conditions that subject the entire content of the waste load to the biocide. During the process some pressure is created releasing small concentrations and amounts of any volatilized chlorine dioxide to the chamber's venting system. An activated carbon filter may be entrained in the ventilation duct to trap any fugitive emissions. The vented chlorine dioxide inactivates bio-aerosols that might escape via this route. Any chlorine dioxide that may escape to the atmosphere will be quickly inactivated by sunlight.

All personnel involved with the operations and maintenance of the Unit will receive training to ensure proper and safe operation of the unit and to ensure the safe handing and disposal of the medical waste treated by the unit. Training will also be conducted on the proper personal protective equipment requirements, chemical storage requirements, chemical use, spill control and containment (chemical and biological), and emergency response (chemical and biological). No one will be allowed to operate, maintain, or repair the unit without proper training or supervision.

All personnel involved with any operation of the Unit will be required to be knowledgeable of the operational and safety processes/procedures.

Critical Factors of the Treatment Process

The critical factor of the treatment process is the amount of organic materials in the medical waste stream and its influence on the chlorine dioxide concentration in the treatment solution. The Unit has been designed and demonstrated to effectively treat a composite medical waste stream consisting of bulk blood, blood products, body fluids, microbiological wastes, sharps waste, and isolation wastes. Waste loads containing excessive amounts of high organic-containing wastes from animals including bedding and carcasses have not been tested to determine treatment conditions required to meet treatment efficacy criteria.

Adverse environmental or occupational effects are also not anticipated in the event of an unanticipated large volume of organic material entering the Unit for treatment. The treatment efficacy results under the established processing times and chlorine dioxide concentrations exceed those criteria recommended in "*Technical Assistance Manual: State Regulatory Oversight of Medical Waste Treatment Technologies*" and the Log reductions acquired in these tests were limited by the initial challenge organism concentrations that could be obtained for the studies (e.g., limited to a 6 $Log_{10}$ spore concentration per test strip). Additionally, the concentrations of challenge microorganisms processed in these studies would exceed those pathogen concentrations typically encountered in a medical waste stream. However to ensure that effective treatment is occurring, biological monitoring will be performed routinely using spore strips containing $1 \times 10^4$ spores of *B. stearothermophilus*. It should also be noted that no occupational contact occurs with the waste or waste residue after the medical waste bag/box is loaded into the unit until the time of automatic discharge into a waste container after all cycles have been completed.

The Unit has been designed to be operator "friendly" through a computer-controlled operating system which provides real time information and operator direction via a visual display on the Master Control Center panel. Intrinsic to the computer-controlled operating system are the process sensors that monitor the Unit to ensure safe and effective operation. These sensors are designed to detect abnormalities that may affect proper waste treatment or unit damage by issuing an operator warning and/or initiating auto shutdown of the entire waste treatment process. The Unit can be safely operated by one individual.

As with any highly mechanized system, routine periodic maintenance schedules are required to ensure that all operating systems will perform as specified without unscheduled interruptions. Routine visual inspections will also occur prior to and during the unit's operation to ensure that all functions not under computer control are operating as specified. These inspections would include a survey of floor areas around and under the unit to check for leaks (i.e., water, treatment solution, lubricating fluids). Additionally the unit would be inspected for any signs of unusual wear of belts or other moving parts. Any repair or any internal inspections will be performed under "Lockout-Tagout" conditions to ensure personnel safety from electrical and physical harm. Properly trained individuals will perform all operations, repair, and maintenance.

The chlorine dioxide generator is virtually maintenance-free. Periodic replacement of 25% sodium chlorite, chlorine (or acid and bleach) and neutralization solution will be required, probably on a once a month to once every 2 month basis.

In the event of a critical malfunction, the Unit has both automatic (computer-recognized and controlled) and operator-controlled emergency shutdown mechanisms. Automatic-controlled emergency mechanisms are initiated by sensors located in strategic control points within the unit and would send an alarm to the computer or operator to initiate auto shutdown procedures. An Emergency Master Switch is also available to initiate immediate and complete shutdown of the unit by the operator if circumstances require. In the event of a malfunction, the unit has been designed to be self-contained to avoid release of chemical or biological contaminants to the area.

The Unit has a fixed treatment cycle time of six minutes to provide adequate chlorine dioxide solution contact time. The addition of the chlorine dioxide solution to the waste load requires approximately four minutes and the neutralization rinse cycle requires approximately two more minutes. With loading and unloading the waste, total turnaround time for a waste load is approximately 20-25 minutes.

Chemical Inactivation Treatment Processes

Chlorine dioxide is the preferred germicidal agent used in the Unit to treat medical waste. Chlorine dioxide can be generated by (1) combining hydrochloric acid with sodium hypochlorite to form chlorine which is subsequently reacted with sodium chlorite or by (2) combining chlorine gas with sodium chlorite. Sodium chlorite is the preferred precursor chemical for use in a medical waste processor or processing method.

The preferred concentration of chlorine dioxide used to inactivate microorganisms is 350 ppm in aqueous solution.

The pH of the treatment solution has little effect on the germicidal activity of chlorine dioxide. Unlike chlorine, chlorine dioxide does not hydrolyze in water and therefore its germicidal activity is relatively constant over a broad pH range. Chlorine dioxide retains its biocidal activity over a pH range of 4-10.

Six minutes has been established as the sufficient processing or contact time through the Unit, although the time may vary depending on the mechanical agitation of the chamber, the physical nature of the medical waste, the particular infectious hazard or hazards in the medical waste to be treated, etc. Should enhanced or shorter time periods for treatment be desired, the introduction of superheated water or low pressure steam can accelerate the treatment process.

The materials of compatibility of chlorine dioxide are well known. Chlorine dioxide is a powerful oxidizing agent and as such will react with reducing agents, oxidizable organic dusts, phosphorous, potassium hydroxide, sulfur, mercuric fluoride, difluoroamine, carbon monoxide, natural rubber seals, carbon steel, copper containing metallurgies, and mercury. The generator has been designed so that all surfaces that the precursors or chlorine dioxide solution contacts is compatible. Little or no apparatus surface corrosion or incompatibility from chlorine dioxide solution is expected during the operative life of the Unit. Hydrochloric acid should always be stored away from the other two precursor chemicals (sodium hypochlorite and sodium chlorite) to avoid a potential dangerous release of chlorine gas or chlorine dioxide if these chemicals were accidentally mixed. Both sodium hypochlorite and sodium chlorite can also be dangerous if allowed to come into contact with reducing agents or flammable materials and as such, require appropriate storage away from these chemicals. Sodium chlorite can also become hazardous if allowed to come into contact with simple organic materials such as wood pallets, rags, etc. In the event of a leak or spill, a potentially flammable powder can result after water evaporation. This material can be self-igniting if exposed to any source of friction, but can remedied by immediately flushing any spill with excessive amounts of water.

The pH of the spent treatment solution is typically expected to be in the range of pH 7 to 9.

The only way that chlorine dioxide could be ineffective is that something is in the water or waste that reacts more rapidly with chlorine dioxide than the chlorine dioxide can react with bacteria. As most of the bacterial activity occurs within the first minute of contact, the only chemical species that could react more rapidly would be some kind of reduced sulfur compound, such as sulfite (the solution used to neutralize the chlorine dioxide solution), or $H_2S$, or sulfide, or any other reduced sulfur compound.

The active life of chlorine dioxide is subject to its rate of decomposition. Although stable under ambient conditions, chlorine dioxide is generated on-site as a liquid just prior to its use to ensure its proper treatment concentration. In the Unit and medical waste treatment process, chlorine dioxide is generated on a per cycle basis to the intended treatment concentration specified to ensure microbial kill. The neutralizing solution will inactivate chlorine dioxide within a few seconds. There is not expected to be any chlorine dioxide remaining in the medical waste after it has been inactivated. In the environment chlorine dioxide in solution is light sensitive. It reacts with light to generate other free radicals ($ClO^-$ and $O^-$) react via a variety of other pathways to form $Cl_2$, chlorine dioxide$^-$, $ClO_3^-$, and $Cl^-$. The decomposition rate of chlorine dioxide solution depends on many factors such as temperature and extreme pH.

There are numerous studies on the long-term effectiveness during use. Chlorine dioxide was used as the bio-terrorism remediation of the anthrax spore release in Washington D.C. in 2001-2002 and is used extensively by laboratory personnel to inactivate the SARS virus in East Asia. Its use as an effective germicide agent is well studied and documented.

Chlorine dioxide is an oxidizing agent and as such, the primary health concern is the oxidative effect that chlorine dioxide may have on body tissues and the blood. Exposures to eyes and skin may cause irritation. The chemical is harmful if swallowed and may be poisonous if inhaled. No effects of carcinogenicity have been reported. OSHA eight-hour time-weighted average Permissible Exposure Limit for "ambient chlorine and chlorine dioxide gas are 1.0 ppm and 0.1 ppm, respectively. The concentrations of chlorine and chlorine dioxide gas considered to be Immediately Dangerous to Life and Health by NIOSH are 30 ppm and 10 ppm, respectively. None of these "breathing zone" standards should ever be exceeded in the workroom area under normal Unit operating conditions. Chlorine dioxide has the potential to become explosive when mixed with air at partial pressure above 80 mm Hg. The intrinsic design of the chlorine dioxide generator used in the Unit will not allow this condition to develop. For additional health and safety information on chlorine dioxide, its precursor chemicals, and neutralization chemicals, refer to Material Data Safety Sheets. It should be emphasized that in the Unit and for the processing system that chlorine dioxide is in aqueous solution and is safe. Chlorine dioxide is used to purify drinking water and chlorite (decomposition product) is used in wound dressings and toothpaste as an antibacterial at concentrations of 1000 ppm.

The active ingredient for the production of chlorine dioxide is sodium chlorite.

Quality Assurance and Verification of Adequate Treatment

The efficacy of the treatment process is a function of chlorine dioxide solution concentration and time of contact. As such, the generation of the chlorine dioxide to the appropriate concentration and delivery volume is critical to the treatment process. The chlorine dioxide solution will be monitored during its generation to insure that a minimum level of chlorine dioxide is delivered to the waste in both concentration and volume. The Unit is also pre-programmed to ensure a treatment (chlorine dioxide contact) cycle is maintained for the duration required for microbial kill. It is expected that under typical conditions for the Unit, about six minutes should be sufficient. Verification of the chemical concentration determined by direct monitoring will be conducted weekly against a standard titration procedure to insure that the instrument remains in calibration. Also weekly, biological spore strip testing will be conducted to correlate biologically that the chemical concentration and contact time is sufficient to effect microbial kill.

Periodic user verification (periodic biological inactivation monitoring) will employ the use of spore strips containing $1 \times 10^4$ spores of *B. stearothermophilus*. Multiple spore strips will be placed within a protective sheath located on one of the cutting blades to monitor the waste treatment efficacy. The spore strips are subsequently processed along with the waste and are retrieved manually from chamber upon discharge of the waste from the unit. Upon retrieval, the spore strips are placed into nutrient media and incubated at 55-60° C. for 48 hours. Growth (demonstrating treatment process inadequacy) is determined by culture media turbidity. If growth occurs in more than one sample, the treatment process and other parametric controls shall be reviewed and the biological indicator test shall be repeated accordingly. If the second test also reveals insufficient microbial inactivation, the unit's use shall be discontinued until the problem is discovered and corrected.

Integral to the chlorine dioxide generation process, is water flow and water pressure that is also monitored to ensure the proper concentration and volumes of solution are delivered to the unit.

The total waste processing system is under microprocessor control to ensure all cycles and their durations are completed with the appropriate amounts of solutions at the proper concentrations. Continuous chlorine dioxide process monitoring will ensure that the proper amounts and concentrations will be delivered to the waste being processed. Independent verification of those processes will be performed weekly to ensure effective microbial kill using biological spore strips.

Treatment efficacy studies have been conducted to correlate the contact time and chlorine dioxide concentration conditions against the efficacy of killing bacterial spore populations. The conditions found to be effective in killing greater than 6 $Log_{10}$ spore populations are those used as standard operation conditions. (See attached treatment efficacy report.)

Monthly, the chlorine dioxide concentration that is monitored instrumentally will be checked against a standard titration procedure to insure that the instrument remains in calibration.

Process monitors have been set to ensure that unless the minimum concentration of chlorine dioxide is applied, the unit will not run.

The unit is pre-programmed to operate at the conditions set by the factory and cannot be overridden by the operator. Additionally the unit will be electronically linked to the corporate office where all functions and operations can be monitored by corporate staff for operational oversight to a unit's performance and as a method of diagnosis for any potential equipment condition(s) that may lead to equipment failure or inadequate waste treatment.

Post-Treatment Residue Disposal, Reclamation or Recycling

Treated waste residues will be placed in dedicated containers for disposal as a general, solid waste in municipal landfills.

It is to be understood that the various steps according to preferred elements of the apparatus and steps of the methods of the invention can be advantageously practiced in various combinations.

Thus, the present invention is well adapted to carry out the objects and attain the ends and advantages mentioned above as well as those inherent therein. While preferred embodiments of the invention have been described for the purpose of this disclosure, changes in the construction and arrangement of parts and the performance of steps can be made by those skilled in the art, which changes are encompassed within the spirit of this invention as defined by the appended claims.

What is claimed is:

1. An apparatus for treating medical waste, wherein the apparatus comprises:
   (i) a drum defining a substantially cylindrical treatment chamber having a closed end and a substantially open end, wherein the drum is rotationally balanced about a rotational axis;
   (ii) an enclosing body supporting the drum so that the drum can be rotated within the body about the rotational axis of the drum, the body having an opening for accessing the open end of the drum, wherein the opening is located substantially in a plane perpendicular to the rotational axis of the drum;
   (iii) a movable barrier for selectively closing the opening for accessing the open end of the drum;
   (iv) a structure for supporting the enclosing body so that the pitch of the rotational axis of the drum is positioned or can be positioned in at least one position between about 0 degrees and about 30 degrees;
   (v) a chemical generator for generating a germicidal agent operatively connected to introduce the germicidal agent into the enclosing body; and
   (vi) an inner movable barrier for selectively closing the open end of the drum, thereby preventing any substantial solids of medical waste from escaping from the treatment chamber during rotation of the drum into the enclosing body outside the drum.

2. The apparatus according to claim 1, wherein the apparatus further comprises: a movable mounting for the enclosing body operatively connected between the support structure and the enclosing body, whereby the pitch of the rotational axis of the drum can be selectively moved.

3. The apparatus according to claim 2, wherein the movable mounting allows the enclosing body to be moved such that the pitch of the rotational axis of the drum is between about 10 degrees and about 30 degrees and such that the opening is oriented at least partially upward to facilitate loading of medical waste at least partially downward into the treatment chamber.

4. The apparatus according to claim 2, wherein the movable mounting allows the enclosing body to be moved such that the pitch of the rotational axis of the drum is between about 10 and about 30 degrees and such that the opening is oriented at least partially downward to facilitate unloading of medical waste at least partially downward from the treatment chamber.

5. The apparatus according to claim 2, further comprising a controller for very slow rotational speed of the drum.

6. The apparatus according to claim 5, wherein the controller for very slow rotational speed of the drum can selectively control the rotation of the drum for less than a single rotation of the drum, whereby the rotation can facilitate loading or unloading of the drum.

7. The apparatus according to claim 1, wherein the apparatus further comprises: a plurality of rotationally-balanced blades positioned inside the drum, whereby when the drum is rotated, the tumbling of the medical waste in the treatment chamber onto the blades ruptures containers and bags of the medical waste.

8. The apparatus according to claim 7, wherein the blades are positioned on an inside wall of the drum.

9. The apparatus according to claim 7, wherein the blades are adapted to rupture disposal containers for needles or syringes that may be present in the medical waste when the drum rotates at a speed to tumble the medical waste in the treatment chamber.

10. The apparatus according to claim 1, wherein the apparatus further comprises: a controller for the introduction of the germicidal agent into the enclosing body in at least a sufficient concentration to achieve "Level IV Microbial Inactivation," wherein the chemical generator is operatively connected to the controller for introducing the germicidal agent.

11. The apparatus according to claim 1, wherein the chemical generator is a chlorine dioxide generator and the germicidal agent is chlorine dioxide.

12. An apparatus for treating medical waste, wherein the apparatus comprises:
  (i) a drum defining a substantially cylindrical treatment chamber having a closed end and a substantially open end, wherein the drum is rotationally balanced about a rotational axis;
  (ii) an enclosing body supporting the drum so that the drum can be rotated within the body about the rotational axis of the drum, the body having an opening for accessing the open end of the drum, wherein the opening is located substantially in a plane perpendicular to the rotational axis of the drum;
  (iii) a movable barrier for selectively closing the opening for accessing the open end of the drum;
  iv an inner movable barrier for selectively closing the open end of the drum, thereby preventing any substantial solids of medical waste from escaping from the treatment chamber during rotation of the drum into the enclosing body outside the drum; and
  (v) a structure for supporting the enclosing body so that the pitch of the rotational axis of the drum is positioned or can be positioned in at least one position between about 0 degrees and about 30 degrees.

13. A method of treating medical waste with an apparatus,
  (A) wherein the apparatus comprises:
    (i) a drum defining a substantially cylindrical treatment chamber having a closed end and a substantially open end, wherein the drum is rotationally balanced about a rotational axis;
    (ii) an enclosing body supporting the drum so that the drum can be rotated within the body about the rotational axis of the drum, the body having an opening for accessing the open end of the drum, wherein the opening is located substantially in a plane perpendicular to the rotational axis of the drum;
    (iii) a movable barrier for selectively closing the opening for accessing the open end of the drum;
    (iv) an inner movable barrier for selectively closing the open end of the drum, thereby preventing any substantial solids of medical waste from escaping from the treatment chamber during rotation of the drum into the enclosing body outside the drum;
    (v) a structure for supporting the enclosing body so that the pitch of the rotational axis of the drum is positioned or can be positioned in at least one position between about 0 degrees and about 30 degrees; and
    (vi) a movable mounting for the enclosing body operatively positioned between the enclosing body and the structure for supporting the enclosing body such that the pitch of the rotational axis of the drum can be selectively moved; and
  (B) wherein the method comprises the steps of:
    (i) moving the enclosing body such that the pitch of the rotational axis of the drum is between about 10 degrees and about 30 degrees and such that the opening is oriented at least partially upward to facilitate loading of medical waste at least partially downward into the treatment chamber;
    (ii) loading medical waste through the opening into the treatment chamber;
    (iii) positioning the movable barrier to close the opening;
    (iv) moving the enclosing body such that pitch of the rotational axis of the drum is between about 0 degrees and about 10 degrees;
    (v) introducing into the treatment chamber a germicidal agent; and
    (vi) rotating the drum to agitate the medical waste with the germicidal agent.

14. The method according to claim 13, wherein the step of moving the enclosing body such that the pitch of the rotational axis of the drum is between about 0 degrees and about 10 degrees further comprises: moving the enclosing body such that the pitch of the rotational axis of the drum is substantially 0 degrees.

15. The method according to claim 13, the method further comprising the steps of:
  (vii) moving the movable barrier to reopen the opening; and
  (viii) moving the enclosing body such that the pitch of the rotational axis of the drum is between about 10 and about 30 degrees and such that the opening is oriented at least partially downward to facilitate unloading of medical waste at least partially downward from the treatment chamber; and
  (ix) unloading the treated medical waste from the treatment chamber.

16. The method according to claim 13, further comprising the step of:
  collecting the medical waste into a bin for transport to the apparatus.

17. The method according to claim 13, wherein the apparatus further comprises: a plurality of rotationally-balanced blades positioned inside the drum, whereby when the drum is rotated, the tumbling of the medical waste in the treatment chamber onto the blades ruptures containers and bags of the medical waste.

18. The method according to claim 17, wherein the blades are adapted to rupture disposal containers for needles or syringes that may be present in the medical waste when the drum rotates at a speed to tumble the medical waste in the treatment chamber.

19. The method according to claim 13, wherein the step of introducing into the treatment chamber a germicidal agent further comprises the step of: introducing a germicidal agent having at least a sufficient effectiveness in at least a sufficient concentration under conditions at least sufficient to achieve "Level IV Microbial Inactivation."

20. The method according to claim 13, wherein the germicidal agent comprises chlorine dioxide.

21. A method of treating medical waste comprising the steps of:
   (i) positioning an enclosing body for a drum such that the pitch of the rotational axis of the drum is upward such that an opening in the enclosing body for accessing the drum is oriented at least partially upward to facilitate loading of medical waste at least partially downward into the drum;
   (ii) loading medical waste through the opening downward into the drum;
   (iii) closing the opening of the drum and closing the opening in the enclosing body;
   (iv) positioning the enclosing body such that pitch of the rotational axis of the drum is substantially horizontal relative to the upward position;
   (v) rotating the drum to agitate the medical waste; and
   (vi) introducing into the enclosing body a germicidal agent to be agitated with the medical waste in the drum.

22. The method according to claim 21, the method further comprising the steps of:
   (vii) re-opening the opening in the enclosing body; and
   (viii) positioning the enclosing body such that the pitch of the rotational axis of the drum is between about 10 and about 30 degrees and such that the opening is oriented at least partially downward to facilitate unloading of medical waste at least partially downward from the drum; and
   (ix) unloading the treated medical waste from the drum.

23. The method according to claim 21, wherein a plurality of rotationally-balanced blades are positioned inside the drum, whereby when the drum is rotated, the tumbling of the medical waste in the treatment chamber onto the blades helps rupture containers and bags of the medical waste.

24. The method according to claim 21, wherein the germicidal agent comprises chlorine dioxide.

25. A method of treating medical waste comprising the steps of:
   (i) positioning an enclosing body for a drum such that the pitch of the rotational axis of the drum is upward such that an opening in the enclosing body for accessing the drum is oriented at least partially upward to facilitate loading of medical waste at least partially downward into the drum;
   (ii) loading medical waste through the opening downward into the drum;
   (iii) closing the opening of the drum;
   (iv) closing the opening in the enclosing body;
   (v) positioning the enclosing body such that pitch of the rotational axis of the drum is substantially horizontal relative to the upward position; and
   (vi) rotating the drum to agitate the medical waste with the germicidal agent, wherein a plurality of rotationally-balanced blades are positioned inside the drum, whereby when the drum is rotated, the tumbling of the medical waste in the treatment chamber onto the blades helps rupture containers and bags of the medical waste.

26. The method according to claim 25, further comprising the step of:
   (vii) introducing into the enclosing body a germicidal agent to be agitated with the medical waste in the drum, wherein the germicidal agent comprises chlorine dioxide.

27. The apparatus according to claim 1, wherein the inner movable barrier for the drum comprises an inner door seal positioned on the movable barrier.

28. The apparatus according to claim 1, wherein the inner movable barrier further comprises a transparent window for viewing inside of the treatment chamber.

* * * * *